(12) United States Patent
Muijs et al.

(10) Patent No.: US 10,240,912 B2
(45) Date of Patent: Mar. 26, 2019

(54) DETERMINING A PROPAGATION VELOCITY FOR A SURFACE WAVE

(71) Applicant: KONINKLIJKE PHILIPS N.V., Eindhoven (NL)

(72) Inventors: Remco Theodorus Johannes Muijs, Meteren (NL); Chris Damkat, Eindhoven (NL); Frederik Jan De Bruijn, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 731 days.

(21) Appl. No.: 14/406,283

(22) PCT Filed: Feb. 11, 2013

(86) PCT No.: PCT/EP2013/052680
§ 371 (c)(1),
(2) Date: Dec. 8, 2014

(87) PCT Pub. No.: WO2013/185937
PCT Pub. Date: Dec. 19, 2013

(65) Prior Publication Data
US 2015/0323311 A1   Nov. 12, 2015

Related U.S. Application Data

(60) Provisional application No. 61/658,986, filed on Jun. 13, 2012.

(51) Int. Cl.
*G01P 3/36* (2006.01)
*G01B 11/16* (2006.01)
(Continued)

(52) U.S. Cl.
CPC .......... *G01B 11/162* (2013.01); *A61B 5/0059* (2013.01); *G01B 9/02095* (2013.01)

(58) Field of Classification Search
CPC .. G01B 11/162; G01B 9/02095; A61B 5/0059
See application file for complete search history.

(56) References Cited

U.S. PATENT DOCUMENTS 5,361,131 A * 11/1994 Tekemori ................ G01P 3/366
356/28.5
5,456,114 A   10/1995 Liu
(Continued)

FOREIGN PATENT DOCUMENTS

| CN | 201503586 U | 6/2010 |
|---|---|---|
| WO | WO2006111836 A1 | 10/2006 |
| WO | WO20130185936 A1 | 12/2013 |

OTHER PUBLICATIONS

Xu M., "Local Measurement of the Pulse Wave Velocity Using Doppler Ultrasound", Dept. of Electrical Engineering and Computer Science, Massachusetts Institute of Technology, May 24, 2002.
(Continued)

*Primary Examiner* — Samantha K Abraham
(74) *Attorney, Agent, or Firm* — Larry Liberchuk

(57) ABSTRACT

An apparatus for determining a propagation velocity for a surface wave comprises a coherent light source (105) for generating at least a first and a second light spot on a surface (103). A camera (111) captures at least one out-of-focus image of at least a part of the surface (103) comprising the light spots. The out-of-focus image comprises light spot image objects for the light spots where the light spot image objects have speckle patterns. An analyzer (113) determines the propagation velocity in response to a time difference between speckle pattern changes in the two speckle patterns. The camera may specifically use a rolling shutter allowing the determination of the propagation velocity to be based on a spatial analysis of the speckle patterns. The approach may
(Continued)

in particular allow an efficient remote measuring of pulse wave velocities e.g. in animal tissue and in particular, in human tissue.

13 Claims, 14 Drawing Sheets

(51) Int. Cl.
  *G01B 9/02* (2006.01)
  *A61B 5/00* (2006.01)

(56) References Cited

U.S. PATENT DOCUMENTS

| | | |
|---|---|---|
| 5,497,662 A | 3/1996 | Dykes |
| 7,113,817 B1 | 9/2006 | Winchester |
| 7,415,880 B2 | 8/2008 | Renzel |
| 2008/0106746 A1 | 5/2008 | Shpunt |
| 2011/0187878 A1* | 8/2011 | Mor .................. G02B 27/0983 348/218.1 |
| 2011/0292406 A1 | 12/2011 | Hollenbeck |
| 2012/0078114 A1 | 3/2012 | Mersch |

OTHER PUBLICATIONS

McLaughlin J et al.,"Piezoelectric Sensor Determination of Arterial Pulse Wave Velocity", Physiological Measurement, Institute of Physics Publishing, Bristol, GB, vol. 24, No. 3, Aug. 1, 2003, pp. 693-702, XP020073714.

Ostberg J E et al., "Vasculopathy in Turner Syndrome", International Congress Series, Excerpta Medica, Amsterdam, NL, vol. 1298, Oct. 1, 2006, pp. 117-122, XP027936962.

Zeev Zalevsky et al.,"Simultaneous Remote Extraction of Multiple Speech Sources and Heart Beats from Secondary Speckles Pattern", Optics Express, vol. 17, No. 24, Nov. 11, 2009, pp. 21566-21580, XP002694988.

* cited by examiner

DETERMINING A PROPAGATION VELOCITY FOR A SURFACE WAVE

FIELD OF THE INVENTION

The invention relates to determination of a propagation velocity for a surface wave e.g. in animal tissue and in particular, but not exclusively, to determining of a propagation velocity for a pulse wave in human tissue. The invention can also be used to estimate other types of wave propagation along the targeted surface, which may find industrial applications, such as vibration monitoring for production equipment.

BACKGROUND OF THE INVENTION

The measurement and monitoring of various properties of animal tissue has become of high importance in many fields. Therefore, there is an increasing desire to provide new or improved methods of measuring characteristics of animal (including human) tissue. In particular, there is a desire to provide methods which allow an easy and practical application with the minimum of inconvenience to the test subject. A particular measurement that is of interest is the measurement of a propagation velocity for a surface wave in animal tissue. Such measurements may provide important indications of various characteristics and may for example assist in the diagnosis or early detection of various health risks.

For example, it is known that high blood pressure is a common risk factor for heart attacks, strokes and aneurysms, and therefore diagnosis and monitoring of this is critically important. Many cardio-vascular diseases originate from a stiffening of the arterial walls, which in turn is related to the blood pulse wave velocity (PWV) via the Moens-Korteweg equation:

$$PWV = \sqrt{\frac{Eh}{\rho d}},$$

where E denotes Young's elasticity modulus of the vessel, h the wall thickness, p the blood density and d the vessel diameter.

A number of methods have therefore been developed to measure blood pulse wave velocity. Due to the relation with the vessel's elastic properties, both invasive and non-invasive methods have been developed. Generally, these involve measuring the passing pressure wave at multiple positions and extracting the velocity of the pulse from the ratio of the displacement and the time delay observed in the recordings. It has been proposed to measure the pressure wave using invasive catheters, mechanical tonometers, Ultrasound Doppler analysis (as disclosed in Xu, M., 2002, "Local measurement of the pulse wave velocity using ultrasound Doppler", Ph.D dissertation, Massachusetts Institute of Technology.), or (piezo-electric) pulse detection devices applied non-invasively to the skin (as disclosed in McLaughlin, J., McNeill, Braun, B and McCormack, P.D, 2003, "Piezoelectric sensor determination of arterial pulse wave velocity", Physiol. Meas. 24, 693-702).

However, the proposed approaches tend to not be optimal. For example, they tend to be inconvenient to the test object (e.g. requiring invasive operations), cumbersome to perform, to provide results that are not as accurate or reliable as would be preferred and/or to require complex and/or costly equipment. In particular, most methods require different sensors to be carefully synchronized to allow the detection of the propagation velocity. Such synchronization tends to be complicated and costly to achieve.

Hence, an improved approach for determining a propagation velocity for a surface wave in animal tissue, and specifically for determining a propagation velocity for a pulse wave, would be advantageous, and in particular a system allowing increased flexibility, reduced resource demand, reduced cost, facilitated implementation, reduced complexity, reduced inconvenience to a test subject, relaxed camera requirements and/or improved performance would be advantageous.

SUMMARY OF THE INVENTION

Accordingly, the invention seeks to preferably mitigate, alleviate or eliminate one or more of the above mentioned disadvantages singly or in any combination. The invention is defined by the independent claims. Advantageous embodiments are defined in the dependent claims.

According to an aspect of the invention there is provided an apparatus for determining a propagation velocity for a surface wave, the apparatus comprising: a coherent light source for generating at least a first light spot and a second light spot on a surface; a camera for capturing at least one out-of-focus image of at least a part of the surface comprising the first and second light spots, the out-of-focus image comprising a first light spot image object for the first light spot, and a second light spot image object for the second light spot, the first light spot image object having a first speckle pattern, and the second light spot image object having a second speckle pattern; and an analyzer for determining the propagation velocity in response to a time difference between speckle pattern changes in the first speckle pattern and the second speckle pattern.

The invention may allow improved and/or facilitated determination of a propagation velocity for a surface wave in animal tissue. In particular, the inventors have realized that such a propagation velocity can accurately be determined using single camera speckle pattern imaging based on a plurality of light spots and associated speckle patterns. The approach can utilize that when illuminating a rough surface with coherent light, minute path length differences in the reflected field result in interference/speckle patterns that can be observed by a defocused camera. The resulting speckle patterns provide a very strong dependency on even small variations in the surface reflecting the light spot, and the inventors have realized that the analysis of two speckle patterns from two different light spots in images from a single camera can be used to provide a very accurate indication of the propagation of a surface wave in animal tissue.

The approach does not require different sensors (or cameras) to be synchronized but allows accurate propagation velocity determination from a single sensor in the form of a single camera capturing both light spots and thus in images comprising two related speckle patterns. Thus, a simultaneous measurement for the two light spots may allow an accurate time determination without requiring synchronization.

It will be appreciated that the surface wave may be any movement in the surface including pulse propagation, and that it is not limited to e.g. specific expanding wave fronts. It will also be appreciated that animal tissue includes both human and non-human tissue; when the invention is used to measure blood pulse wave velocity it can be used with any animal having a blood pulse, e.g. dogs or other mammals.

The coherent light source may in many embodiments be a laser light source arranged to generate laser light spots on the surface. The coherent light source may be focused on the surface so as to provide sufficiently small light spots, typically with an area of less than 2 mm$^2$, and often preferably less than 1 mm$^2$. The apparatus may in particular be arranged to generate a relatively coarse speckle pattern, and in particular the coherent light source may generate the light spot to be sufficiently small to result in an average speckle grain size of at least 10 square pixels.

The two light spots are spatially separated. The distance may typically be no less than 2 cm, but in many cases preferably no less than 5 cm, or even no less than 10 cm or 15 cm.

The camera may be a lens-less camera.

In accordance with an optional feature of the invention, the analyzer is arranged to: determine a first property of the first speckle pattern; determine a second property of the second speckle pattern; detect a first change in the first property; detect a second change in the second property; and determine the propagation velocity in response to a time difference between a time instant of the first change and a time instant of the second change. This may provide a particularly advantageous determination of the propagation velocity. In particular, it may provide for a low complexity, yet reliable and accurate determination of the propagation velocity.

The change may specifically be a step change. A detection requirement may be that a change in the value of a property crosses a given threshold. For example, if the properties are speckle pattern contrasts, the change may be detected to occur when the speckle contrast changes by more than a predetermined amount, or if it crosses a predetermined threshold value.

In accordance with an optional feature of the invention, the camera comprises a rolling shutter for capturing the at least one out-of-focus image. This may in particular allow improved, facilitated, and/or reduced complexity determination of the propagation velocity. In particular, it may in many embodiments allow improved trade-off between temporal resolution and camera requirements. Specifically, in many embodiments the need for high speed cameras can be mitigated or obviated while still achieving the high temporal resolution associated with such cameras. The approach may allow determination of high frequency variations without requiring high frame rate cameras. The approach may reduce implementation costs very substantially as the cost reduction associated with e.g. normal frame rate cameras relative to high frame rate cameras is very substantial. Furthermore, in many embodiments simplified or improved processing can be achieved allowing an improved trade-off of performance versus complexity and resource usage.

The rolling shutter effect may be used to convert temporal characteristics of the surface of the animal tissue into spatial characteristics of the resulting speckle patterns, and this may further be analyzed to estimate the propagation velocity. In particular, a temporal resolution which exceeds the temporal resolution of the camera used to capture the out-of-focus image can be achieved thereby allowing a more accurate determination of the propagation velocity. The approach may in particular allow an accurate time difference determination between speckle pattern changes for different light spots as it may allow a single image to provide corresponding/synchronized temporal information for both speckle patterns. It may in particular obviate the requirement for synchronization as both measurement points are measured by the same sensor equipment and with the same temporal characteristics. Thus, a single image may in many scenarios provide not only a spatial representation of the temporal characteristics but also inherently provide a synchronization of the measurements for the two light spots.

In accordance with an optional feature of the invention, the analyzer is arranged to determine the time difference in response to a spatial comparison of the first speckle pattern and the second speckle pattern in one out-of-focus image. This may provide a particularly advantageous determination and may in particular facilitate the analysis. The transformation of temporal characteristics into spatial characteristics provided by the rolling shutter may be used to provide an improved determination of the time difference.

In accordance with an optional feature of the invention, the analyzer is arranged to determine the time difference in response to a spatial correlation of the first speckle pattern and the second speckle pattern. This may provide a particularly advantageous determination and may in particular facilitate the analysis. The transformation of temporal characteristics into spatial characteristics provided by the rolling shutter may be used to provide an improved determination of the time difference.

In accordance with an optional feature of the invention, the analyzer is arranged to determine the time difference in response to a spatial pattern variation for the first speckle pattern and the second speckle pattern in a direction corresponding to the rolling shutter propagation direction. This may provide a particularly advantageous estimation of a propagation velocity.

The rolling shutter may perform a line sequential operation where it performs a time sequential capturing of lines. The capturing of the image may be achieved in a plurality of sequential time intervals wherein only a subset of lines is captured in each time interval (often a single line). The rolling shutter will thus have a propagation direction perpendicularly to the line direction. Depending on the orientation of the rolling shutter, the lines may typically be considered to correspond to rows or columns of the image.

In accordance with an optional feature of the invention, the analyzer is arranged to determine the time difference in response to a spatial offset between pattern changes in the first speckle pattern and the second speckle pattern. This may provide a particularly advantageous estimation of a propagation velocity. A reliable yet low complexity spatial analysis may allow corresponding pattern changes or transitions to be detected. The position of these transitions in the out-of-focus image is an indication of the timing of the change, and thus an indication of the timing of the surface wave at the two light spots. Thus, the analyzer may calculate the time difference from the spatial distance (in the rolling shutter direction) between the two pattern transitions and knowledge of the rolling shutter speed.

In accordance with an optional feature of the invention, the rolling shutter is arranged to capture the out-of-focus image line sequentially; and the analyzer is arranged to: determine a first speckle pattern property for the first light spot image object for each group of a plurality of groups which each comprise at least part of a number of adjacent lines of the out-of-focus image; determine a second speckle pattern property for the second light spot image object for each group of the plurality of groups; detect a first change of the first pattern property between groups of the plurality of groups; detect a second change of the second pattern property between groups of the second plurality of groups; and determine the time difference in response to a spatial difference between the first change in the first light spot image object and the second change in the second light spot image object. This may provide a particularly advantageous estimation of a propagation velocity.

In accordance with an optional feature of the invention, the analyzer is arranged to determine the time difference in response to a spatial offset between changes in speckle contrast for the first light spot image object and the second light spot image object. This may provide a particularly advantageous estimation of a propagation velocity. In particular, it may provide a reliable, yet low complexity determination of the time difference. The analyzer may specifically be arranged to determine a speckle contrast for each line of the first and second light spot image objects, to detect a change in the line speckle contrast for each of the first and second light spot image objects, and to determine the time difference in response to a spatial offset between the relative positions of the detected changes in the first and second image objects.

The speckle contrast may specifically be a line speckle contrast, and the analyzer may specifically be arranged to determine the time difference in response to a spatial offset between corresponding changes in line speckle contrast for the first light spot image object and the second light spot image object.

In accordance with an optional feature of the invention, the analyzer is arranged to determine the time difference in response to a spatial offset between changes in inter-line speckle pattern displacements for the first light spot image object and the second light spot image object. This may provide a particularly advantageous estimation of a propagation velocity. The inter-line speckle pattern displacement may be an estimated displacement between the speckle patterns of two adjacent lines.

The approach may in particular provide a reliable, yet low complexity determination of the time difference. The analyzer may specifically be arranged to determine a displacement for each line of the first and second light spot image objects relative to the previous line, to detect a change in the line displacement for each of the first and second light spot image objects, and to determine the time difference in response to a spatial offset between the relative positions of the detected changes in the first and second image objects respectively.

In accordance with an optional feature of the invention, the coherent light source is arranged to generate a plurality of light spots on the surface and the camera is arranged to capture the plurality of light spots in the out-of-focus image; and further comprising: a selector arranged to select a subset of light spots for analysis by the analyzer. This may facilitate and improve operation for many applications and may in many embodiments provide an improved determination of the propagation velocity. Specifically, the approach may allow light spots in particularly suitable positions on the surface to be used for the determination. The approach may in particular allow for the speckle pattern velocity determination to be used more flexibly and in applications with higher degrees of variability, not least in terms of the positioning of the animal tissue. For example, if used for determining a propagation velocity for a surface wave of a patient, the approach may allow a suitable area for the determination to be determined without requiring the patient to be positioned with extreme accuracy. Improved analysis may often be possible as the light spot resulting in the speckle pattern with the best characteristics (e.g. the highest speckle pattern contrast) can be used.

The subset of light spots comprises the first and second light spots, and indeed in some embodiments the subset may consist of the first and second light spots. In some embodiments, the selector is arranged to select the first and second light spots from the plurality of light spots.

The plurality of light spots may form a regular or irregular grid of light spots. The light spots may preferably be arranged to be non-overlapping in the out-of-focus image. The coherent light source may comprise a plurality of light sources, such as a laser for each light spot.

In accordance with an optional feature of the invention, the selector is arranged to select the subset of light spots using a lower processing resolution than used by the analyzer when determining the propagation velocity. This may reduce complexity and/or resource usage yet may provide a reliable and high performance detection of suitable light spots for the analysis.

In accordance with an optional feature of the invention, the selector is arranged to select the subset in response to at least one of: an intensity for light spots of the plurality of the light spots; a speckle contrast for light spots of the plurality of the light spots; a speckle pattern variation for light spots of the plurality of the light spots; a correlation between variations for different light spots of the plurality of the light spots; and a change in a light spot pattern of the plurality of the light spots. This may provide particularly advantageous selection of a subset of light spots for use in the speckle pattern velocity determination. In particular, it may in many embodiments result in an improved determination of the surface wave propagation velocity as it may allow light spots with particularly suitable speckle patterns to be used for the determination.

In accordance with an optional feature of the invention, the apparatus is arranged to determine a propagation velocity for a pulse wave.

The invention may allow an improved determination of a pulse wave velocity and in particular may allow a reduced complexity determination which does not require sensors to be attached to or inserted into the patient, and which further does not require accurate synchronization or complex signal processing.

According to an aspect of the invention, there is provided a method of determining a propagation velocity for a surface wave, the method comprising: generating at least a first light spot and a second light spot on a surface; capturing at least one out-of-focus image of at least a part of the surface comprising the first and second light spots, the out-of-focus image comprising a first light spot image object for the first light spot, and a second light spot image object for the second light spot, the first light spot image object having a first speckle pattern, and the second light spot image object having a second speckle pattern; and determining the propagation velocity in response to a time difference between speckle pattern changes in the first speckle pattern and the second speckle pattern.

These and other aspects, features and advantages of the invention will be apparent from and elucidated with reference to the embodiment(s) described hereinafter.

BRIEF DESCRIPTION OF THE DRAWINGS

Embodiments of the invention will be described, by way of example only, with reference to the drawings, in which.

DETAILED DESCRIPTION OF SOME EMBODIMENTS OF THE INVENTION

The following description focuses on embodiments for measuring propagation velocity for a surface wave in animal tissue, including human tissue. Specifically, the inventors have realized the approach can be used to determine a propagation velocity for a pulse wave. In particular, the following description will focus on systems which allow an efficient, accurate, reliable, flexible and easy determination of propagation velocity for a pulse wave in a human patient. The system in particular provides measurements that may be very significant for evaluating, detecting and diagnosing many cardio-vascular diseases.

Figure 1:
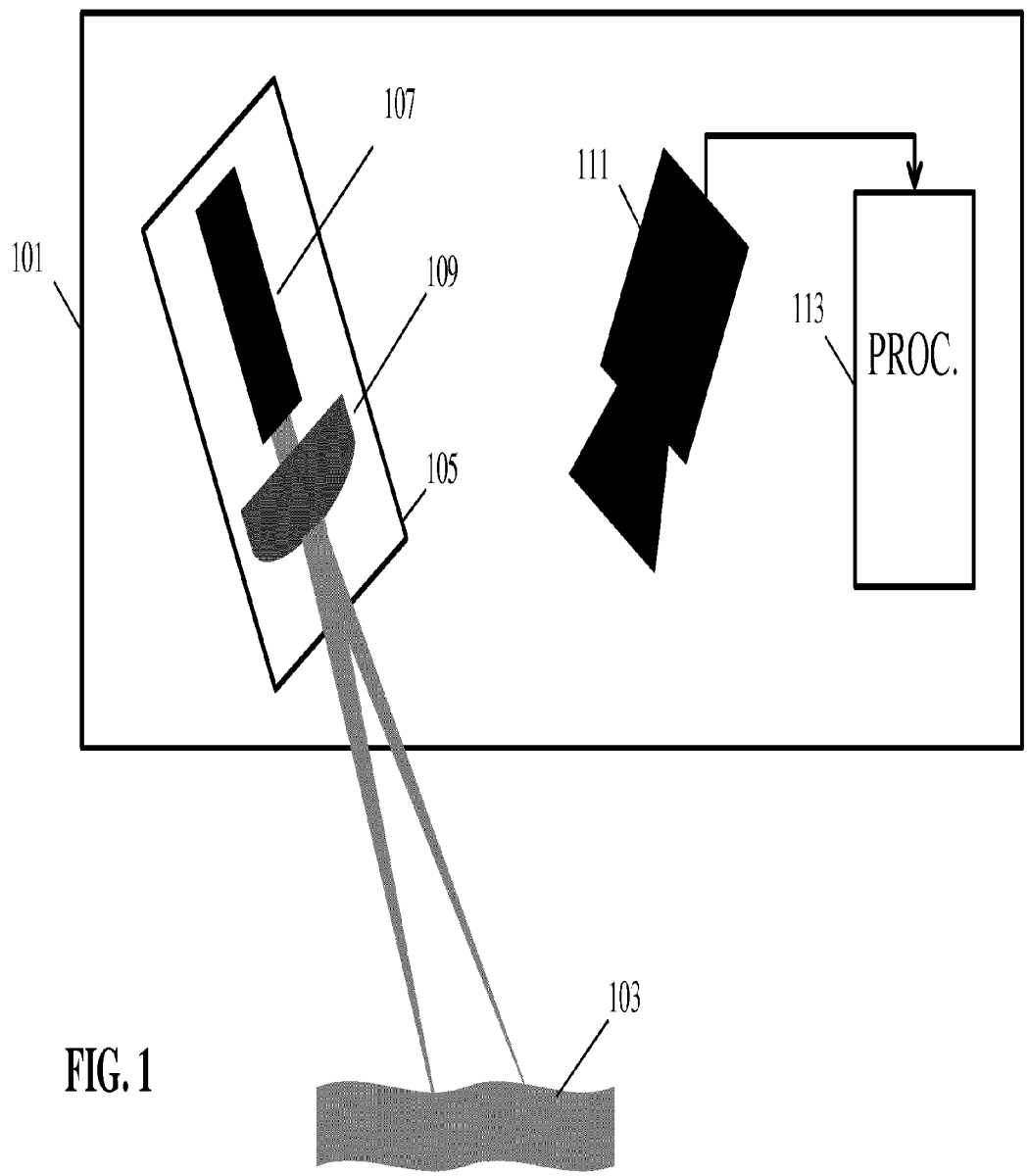
FIG. 1 illustrates an example of a speckle imaging apparatus in accordance with some embodiments of the invention.

FIG. 1 illustrates an example of a pulse wave propagation velocity measurement setup in accordance with some embodiments of the invention.

The setup comprises a speckle imaging apparatus 101 which is arranged to determine the pulse wave propagation velocity by performing speckle imaging from at least two speckle patterns which are projected onto a part of the patient's body. When the blood pulse propagates through the body, it results in small disturbances and distortions in the skin surface on many parts of the body. The speckle imaging apparatus 101 of FIG. 1 is arranged to detect such small variations at at least two positions on the surface of the patients skin, and to estimate the pulse wave propagation velocity based on this. Accordingly, the speckle imaging apparatus 101 generates at least two light spots on suitable positions of the surface 103 of the body of the patient. Each light spot is imaged to create a speckle pattern and the speckle patterns are analyzed to generate a pulse wave velocity estimate.

The speckle imaging apparatus 101 comprises a coherent light source 105 which is arranged to generate at least two spots on the surface 103. In the specific example, the coherent light source 105 is a laser light source, and it comprises a laser 107 and a lens 109 which is capable of focusing the laser light source on the surface 103 such that sufficiently small light spots are generated on the surface 103. Of course, the lens may not be necessary in all embodiments and especially not for embodiments wherein e.g. a laser light source can generate sufficiently small light spots.

The coherent light source 105 may for example generate the two or more light spots by the use of multiple laser light sources, a single source with a diffraction grating, or the use of beam splitters and mirrors.

The speckle imaging apparatus 101 further comprises a camera 111 which is arranged to capture an image of (at least part of) the surface 103 including at least two light spots generated by the coherent light source 105. The camera 111 is arranged such that it captures an out-of-focus image of the surface 103, i.e. the camera is arranged to capture the image with a focal plane that differs from the surface 130. Thus, the focus distance for the camera differs from the distance from the surface 103 to the camera 111 when the apparatus is in use. In some embodiments, the camera may be a camera without any focusing lens. Indeed, a lens-less camera corresponding to a bare sensor may be used in some embodiments. Indeed, such a camera can be considered a special case of unfocused imaging with the focus being on the sensor itself.

The camera 111 is accordingly arranged to have a focus distance that is different from the distance from the camera 111 to an operating distance range in which the object may be positioned. It will be appreciated that the specific distances involved, the positioning of the surface etc. may depend on the individual application etc. Furthermore, it will be appreciated that the actual design and implementation of the speckle imaging apparatus 101 does not rely on the surface 103 being present or at a specific position. Rather, the speckle imaging apparatus 101 may be designed for the surface 103 to be positioned within a given operating volume/distance range. The coherent light source 105 and the camera 111 may then be arranged to provide acceptable performance when an object is positioned with the surface to be monitored within this operating volume/distance range.

Typically, the focus distance of the camera 111 will be at least twice, and often at least five times, the maximum distance of the operating distance interval. The operating distance interval is the interval for which the speckle imaging apparatus 101 has been designed, i.e. it is the range in which the surface 103 should be placed when the apparatus is in use.

It will be appreciated that in some embodiments, the speckle imaging apparatus 101 may be arranged to manually or automatically adapt to a specific positioning of the surface 103. For example, the focusing of the light from the coherent light source 105 can be manually adjusted by changing the distance between the laser 107 and the lens 109. As another example, the adjustment may be automatic and may be based on a feedback loop which minimizes the spot size of the light spot on the surface 103. Similarly, the focusing of the camera 111 may be manually adjustable or may be automatically adjustable (for example based on a feedback system which maximizes the size of the image object corresponding to the light spot, or which maximizes the speckle pattern contrast). In other embodiments, the focus may be constant. For example, the camera 111 may be set to have an infinite focus distance.

The system of FIG. 1 is based on speckle imaging. Speckle imaging exploits that when illuminating a rough surface with coherent light, minute path length differences in the reflected field result in interference/speckle patterns that can be observed by a defocused camera. The coherent light is typically generated by a laser light source. A speckle pattern may be thought of as a random intensity pattern produced by the mutual interference of a set of wave-fronts. Analysis of these patterns and their dynamic behavior allows for high-precision detection of, for example, target translation and rotation, flow parameters and material characterization. Over the years, speckle imaging has found diverse applications in industrial metrology, medical applications, material characterization, vital signs analysis, blood flow measurements, measurements of small displacements and many more.

Laser-speckle imaging enables distant, contactless measurement of very small surface motion, such as induced by sound or by vital signs (heart-beat, respiration), or of very distant motion such as a handheld remote interaction device (game controller, pointing device).

An approach to speckle imaging is to use a laser which is focused on a surface to generate a small spot on the surface. An image of the spot is captured using an imaging objective which is defocused. Defocusing of the camera results in a "circle of confusion" or "blur circle". Due to the coherent nature of the light from the laser, this circle is not uniform in intensity, but rather contains a speckle pattern caused by interference between different wave-fronts. The speckle pattern is dependent on the surface which reflects the laser light. In particular, the roughness and small variations in the surface texture result in varying phase dependencies of reflected wave-fronts which result in the interference speckle pattern. Furthermore, small movements of the object surface will be visible in the speckle pattern as translations. A particular advantage of speckle imaging is that the object motion is highly amplified in the translation of the speckle pattern thereby making it practical to detect even very small movements. In practice, even a small change in the position or orientation of a laser-illuminated surface gives rise to large displacements of the associated speckle field. In addition, if the motion contains temporally high-frequent variations, the associated speckle field will exhibit the same temporal frequency characteristics.

These characteristics have for example been used by to measure heart beats and speech at a large distance (several meters or more) by use of a collimated laser and a defocused camera as disclosed in Zeev Zalevsky, Yevgeny Beiderman, Israel Margalit, Shimshon Gingold, Mina Teicher, Vicente Mico, and Javier Garcia, "Simultaneous remote extraction of multiple speech sources and heart beats from secondary speckles pattern", Optics Express, Vol. 17, Issue 24, pp. 21566-21580, 2009.

In the setup of FIG. 1, the image object of the light spots generated by the coherent light source 105 will comprise a speckle pattern due to the defocussing of the camera 111. Thus, the defocusing of the camera 111 results in an image object for each light spot which contains the interference/speckle pattern. This interference results from the phase variations between different waveform reflections caused by slight variations in the surface of the human tissue under test. Thus, whereas the incident light is coherent, the surface variations results in the reflected waves having differing phases, and by capturing a defocused image these variations result in an interference pattern.

In the speckle imaging apparatus 101 of FIG. 1, the camera 111 is coupled to an analysis processor 113 which proceeds to determine a propagation velocity based on the speckle patterns generated by the camera 111. The analysis processor specifically determines the propagation velocity in response to a time difference between corresponding speckle pattern changes in the two captured speckle patterns In typical embodiments, the coherent light source 105 will be arranged to provide light spots with a total area of no more than 1 mm², and often advantageously significantly smaller such as no more than 0.5 mm², or even no more than 0.1 mm². Thus, when the surface 103 is within the operating interval, the coherent light source 105 can provide such small light spots (either fixedly or using manual and/or automatic adaptation).

It will be appreciated that the observed speckle size is not only dependent on the light spot size but also depends on other parameters, such as observation distance, imaging optics and physical sensor resolution. Typically, it is however more practical to control the light spot size.

Although the light spots generated by the coherent light source 105 would appear as small dots in a focused image of the surface 103, the corresponding image objects for images captured by the defocussed camera 111 become relatively large (typically circular) areas with distinct and sharp speckle patterns. The size of the speckle pattern is determined by the object distance in relation to the (de)focus distance, which can be infinity. The larger the difference between object distance and focus distance, the larger the area that is filled with the speckle pattern.

The spatial frequency bandwidth of the speckle pattern, which determines the granularity of its appearance, is determined by the size of the illuminated spot. The smaller the illuminated spot, the smaller the spatial frequency bandwidth, and the coarser the speckle grains.

Figure 2:
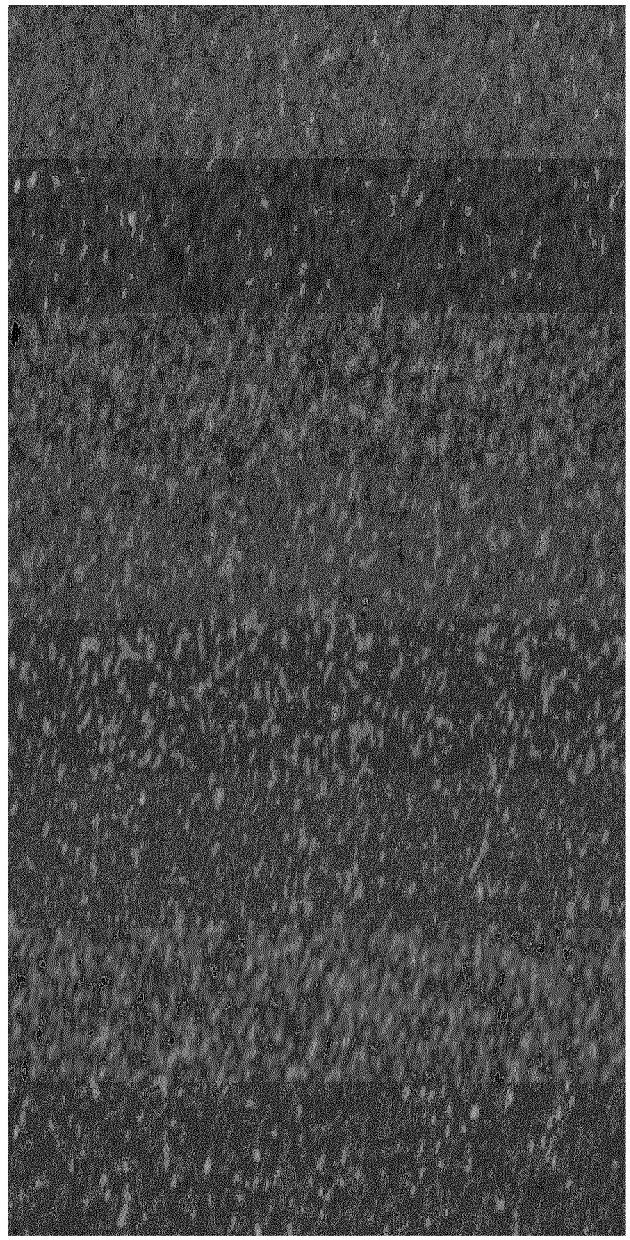
FIGS. 2 to 7 illustrate examples of speckle patterns.

An example of a speckle pattern is illustrated in FIG. 2.

The speckle imaging apparatus 101 of FIG. 1 exploits the fact that a surface wave results in small variations in the distance to the surface as the surface wave moves across the surface. Thus, at a given point the surface characteristics will change as the wave front of the surface wave/pulse passes. The system exploits the fact that this change results in a change in the speckle pattern resulting from the reflection of the individual light spot. Thus, by detecting a speckle pattern change a detection of the surface wave passing the light spot can be achieved. In the system of FIG. 1, speckle pattern changes are detected for two light spots that are spatially separated. The time difference is determined between the two speckle pattern changes and this time difference is considered indicative of the time it takes the surface wave/pulse to travel from one light spot to the other. Accordingly, the surface wave velocity is calculated from the time difference and the distance between the light spots.

The system thus detects corresponding minor surface disturbances and variations that occur as the surface wave/pulse propagates to two different points on the surface. In the specific example where the blood pulse wave velocity is measured, the light spots may illuminate proximal positions in the immediate vicinity of the same arteries in e.g. the upper arm or wrist. Typical distances between the light spots may for example be between 1 cm and 20 cm, and typically advantageously no less than 3 cm and no more than 10 cm.

The speckle pattern changes may be detected in accordance with a suitable criterion. Specifically, the analysis processor 113 may determine a property for each of the two speckle patterns. Typically, the same property will be determined for both speckle patterns but in some embodiments, the specific property which is evaluated may be different for the two patterns. The specific property which is evaluated will depend on the preferences and requirements of the individual embodiment. In many embodiments, the property may advantageously be a speckle pattern contrast or e.g. a displacement between consecutive patterns.

The analysis processor 113 then proceeds to detect a change in each property in accordance with a suitable change detection criterion. For example, the analysis processor 113 may detect that the value of the property changes by more than a given level in a given time interval, that the property deviates by more than a predetermined level from a nominal, default or time averaged value, etc.

The time difference between the two detected changes is then determined and based on the time difference the pulse wave velocity is calculated. Specifically, the pulse wave velocity PWV can be calculated as the ratio between the distance between the light spots $\Delta r_{dot}$ on the measured surface and the estimated time delay $\Delta t$:

$$PWV = \frac{\Delta r_{dot}}{\Delta t}.$$

In some embodiments, the analysis may be performed on a sequence of images, and specifically the camera 111 may be a video camera providing a video signal comprising a sequence of frames/images.

In such an example, the analysis processor 113 may determine a single value of the property, such as e.g. a speckle contrast, for each speckle pattern in each image. As the pulse wave moves across the surface, this will first cause a deviation in the surface at the first light spot resulting in the speckle contrast for the corresponding speckle contrast changing. Thus, for an image captured at the time instant when the surface wave moves across the first light spot, but not yet having reached the second light spot, the speckle pattern of the first light spot undergoes a change whereas the speckle pattern of the second light spot does not. At some time later, the surface wave reaches the second light spot and the second speckle pattern undergoes a chance. The time difference between the surface wave passing the first light spot and the surface wave passing the second light spot can then be determined as the time difference between the corresponding images. As a simple example, the time difference may be determined as the frame time multiplied by the number of frames between the frame in which the first speckle pattern is detected to have changed to the from in which the second speckle pattern is detected to have changed. The pulse wave velocity can then be determined as described above.

The system of FIG. 1 is accordingly arranged to determine the surface wave velocity from images that comprise speckle patterns for both light spots. This provides a significant advantage as it can avoid or reduce the need for synchronizations of measurements for different positions and accordingly it provides a lower complexity implementation and/or more reliable velocity determination.

Although such an approach may lead to accurate surface wave velocity measurements for many embodiments, it requires the camera to have a sufficiently high frame rate to allow the inter-frame time differences to be sufficiently short to provide sufficient temporal resolution to result in a sufficient resolution for the velocity estimates.

In order to measure fast velocities with sufficient resolution/accuracy, high speed cameras must accordingly be used. This typically increases cost very substantially. In addition, the need to analyze speckle patterns for many images tends to result in complex and resource demanding applications.

In some embodiments these disadvantages may be mitigated. Specifically, in some embodiments the camera 111 may comprise a rolling shutter with the out-of-focus images (or indeed single out-of-focus image) being captured using a rolling shutter capture.

Rather than use a traditional camera wherein the image is created by sensing light in the same time interval for all parts of the image, the camera 111 of the speckle imaging apparatus 101 of FIG. 1 uses a time offset sampling of different areas of the image in such embodiments. Thus, the image may be divided into a plurality of areas having capture instants that are offset relative to each other. Accordingly, the sampling instants are not constant for all pixels of the image but rather vary across the image.

As a specific example, the rolling shutter may capture the image in a line sequential manner. Specifically, it may generate the image one line at a time with the sampling/capture instant being offset for each line. Thus, the actual capture instant will increase for each line. In many embodiments, the image may be generated by the camera sampling the outputs of an imaging sensor (such as a charge coupled device CCD sensor). The rolling shutter may specifically result in a line by line capture and may be implemented by each line of the imaging sensor being sampled substantially simultaneously but with a time offset between the lines. Thus, the lines may be sampled sequentially, one line at a time (or possibly N lines at the time where N is an integer).

The resulting image will accordingly reflect the surface at slightly different times since each line will correspond to a different sample instant. As a consequence, the speckle patterns do not just represent characteristics of the surface at one single time instant but also contains temporal information, i.e. each speckle pattern may also reflect how the surface property at the position of the corresponding light spot varies over time.

The following description will focus on embodiments wherein a line sequential rolling shutter is implemented. Thus, in the example, the propagation direction of the rolling shutter will be in the perpendicular direction to the line direction. For example, when the rolling shutter reads one row at a time (i.e. a line of the line sequential operation corresponds to a row of pixels of the image sensor), the propagation direction is in the column direction. Similarly, if the rolling shutter reads one column at a time (i.e. a line of the line sequential operation corresponds to a column of pixels of the image sensor), the propagation direction is in the row direction. The following descriptions will focus on examples wherein the rolling shutter reads one horizontal row at a time, and thus where the propagation direction for the rolling shutter is in the vertical direction.

It will be appreciated that in other embodiments, the rolling shutter may read more than one line at a time, or that it may be arranged in other directions. For example, in some embodiments the rolling shutter may have a diagonal propagation direction, and it may thus sample the image sensor in lines that are perpendicular to this diagonal (i.e. parallel to the opposite diagonal for a square sensor). It will be appreciated that the propagation direction corresponds to the direction from the area (e.g. center point) being sampled at a given sample instant to the area (e.g. center point) being sampled at the next sample instant.

The analysis performed by the analysis processor 113 is arranged to determine the time difference between the time instants of a passing surface wave at the two light spot locations based on an analysis which takes into account the relationship between spatial and temporal characteristics of the captured image. In particular, the camera exploits the Inventors' realization that a rolling shutter introduces a temporal effect to the spatial image properties and that by analyzing the spatial image properties (even in a single image) information of temporal characteristics can be obtained.

The approach of using a rolling shutter may in particular mitigate or obviate the need for high speed cameras. Indeed, a temporal resolution of the determined property which is substantially higher than the image frame rate can be achieved. Indeed, in many applications, a temporal resolution no less than ten times higher than the frame rate of the image can be achieved.

Also, the system may reduce complexity and resource demand of the required processing in many embodiments. Indeed, the transformation of temporal characteristics into spatial characteristics of a spatial pattern in a single image may not only reduce the resource demand due to the need to analyze fewer pictures but may in addition allow many low complexity algorithms to be used. In particular, a number of spatial analysis algorithms may be less resource demanding than algorithms based on temporal analyses between different images.

Figure 3:
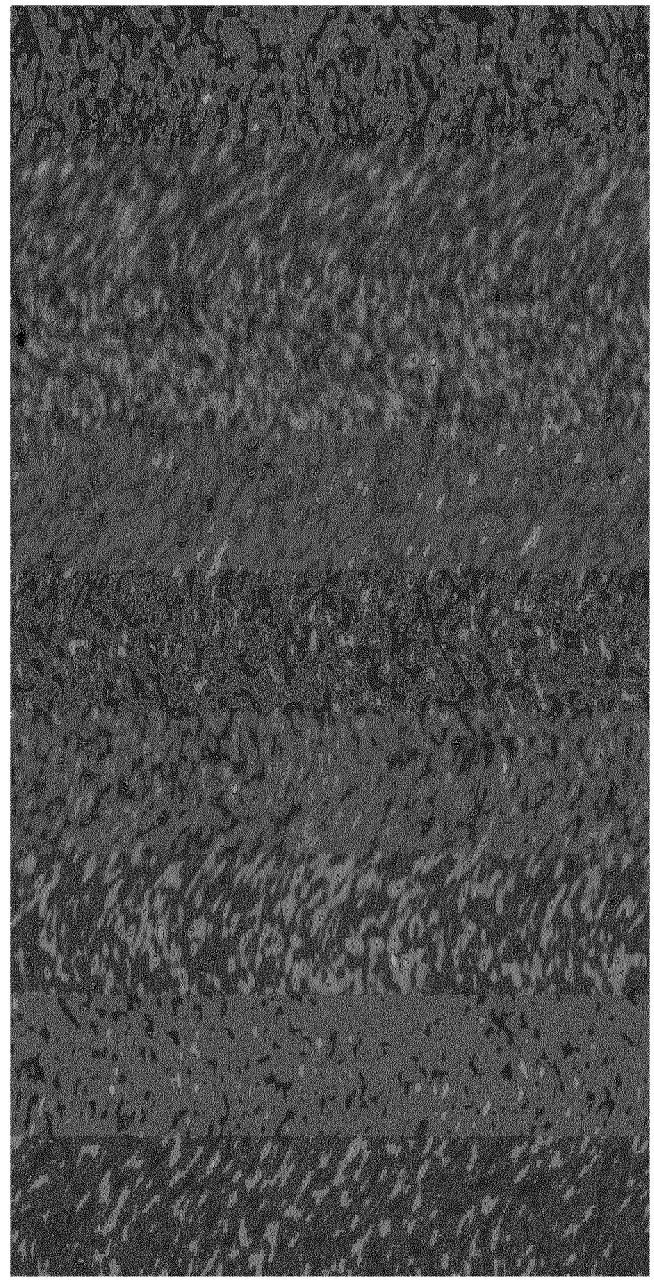

An example of a speckle pattern for a moving surface captured by a camera using a rolling shutter approach is illustrated in FIG. 3. As can be seen, the speckle pattern exhibits a spatial pattern variation which reflects how the pattern translates between the different sampling instants. In the specific example, a vibrating motion is introduced to the surface and as can be seen this results in a spatial pattern with translations in the horizontal direction as a function of the vertical position. In the example, the rolling shutter is row sequential and accordingly the vertical direction of the pattern also reflects a temporal dimension. Specifically, the pattern of FIG. 3 exhibits vertical waves corresponding to the sinusoidal vibrations of the surface. The horizontal translations as a function of vertical positions thus provide information of the temporal variation of the surface, and specifically of the movement of the surface.

Figure 4:
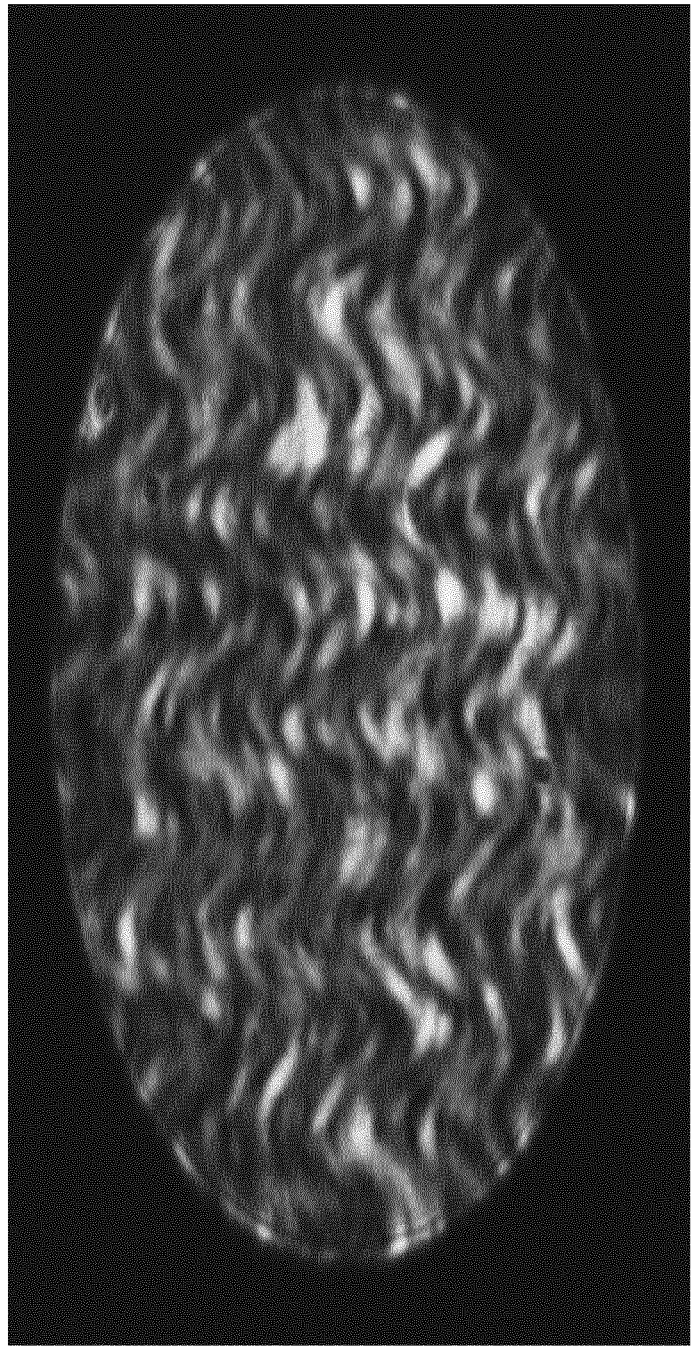
Figure 5:
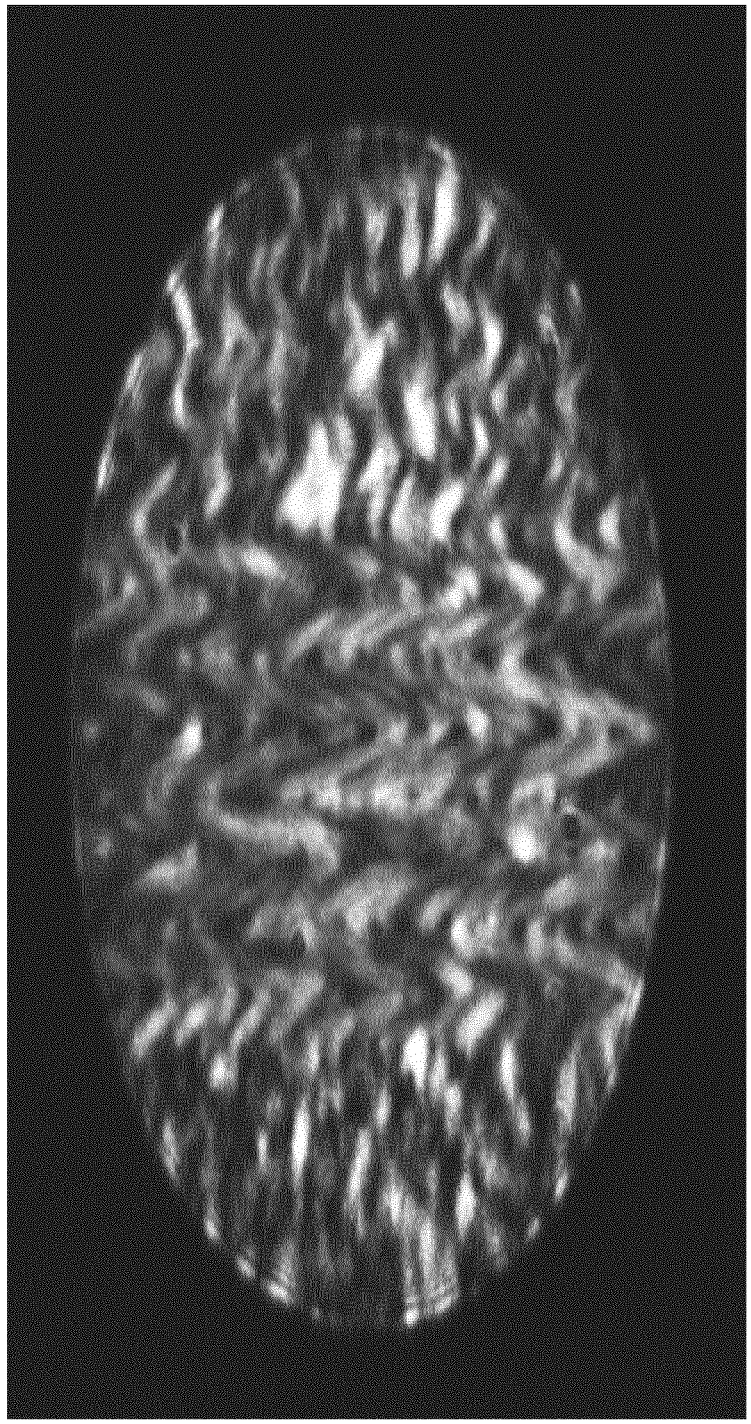

Other examples of speckle patterns having spatial characteristics reflecting the movement of a surface are illustrated in FIGS. 4 and 5. FIG. 4 illustrates an example wherein the surface has a movement corresponding to a sinus wave with a frequency of 246 Hz, and FIG. 5 illustrates an example wherein the surface is subject to a short pulse with associated vibrations.

The analysis processor 113 is arranged to exploit the spatial representation of the temporal variations of the surface to determine the time difference between the surface wave (or pulse) passing the first and second light spots. Thus, the analysis processor 113 can perform a spatial analysis on the speckle patterns and can use this to determine a time difference which subsequently is used for calculating a wave velocity. The analysis processor 113 is arranged to analyze how the spatial speckle pattern varies in the spatial direction reflecting the time variation, i.e. in the direction of propagation of the rolling shutter. Thus, in the specific example, the variation between speckle patterns at different vertical positions is analyzed.

In systems using a rolling shutter, the analysis processor 113 may accordingly determine the time difference in response to spatial characteristics of the two speckle patterns. Specifically, the time difference may be determined in response to a spatial correlation of the first speckle pattern and the second speckle pattern. For example, the two patterns may be spatially correlated and a spatial shift or offset corresponding to a maximum correlation may be determined. This spatial difference may then be converted to a time difference by taking into account the speed of the rolling shutter. For example, if the maximum correlation is found for an offset of, say, eight lines, the time difference may be determined as eight times the line-to-line time of the rolling shutter. The time difference may thus be determined by a spatial comparison of the speckle patterns for the first light spot and the second light spot.

It will be appreciated that the analysis processor 113 may use different algorithms for determining the time difference. A number of approaches will be described in the following. However, it should be appreciated that the analysis processor 113 is not limited to these examples but that other approaches may be used in other embodiments dependent on the specific preferences and requirements of the individual embodiment.

In some embodiments and scenarios, the analysis processor 113 may be arranged to determine time difference in response to a spatial comparison of the first speckle pattern and the second speckle pattern in one out-of-focus image.

When the wave front of a surface wave passes a light spot, it will result in a movement of the surface which results in a change in the speckle pattern. For a rolling shutter capture this will result in a change in the speckle pattern at the spatial location which corresponds to the tine of the wave front passing. Thus, the captured speckle pattern will exhibit a change in the pattern characteristics with the spatial position of the change directly representing the time of the wave front passing. This phenomenon will occur for both light spots image objects, i.e. for light spots. However, as the light spots are spatially offset the exact time of the change will be different and this will result in the change occurring at different spatial positions. If the two light spots are sufficiently close for the time difference between the wave fronts passing the light spots to be within a single frame capture interval, both image objects in a single image may exhibit a speckle pattern change.

Figure 6:
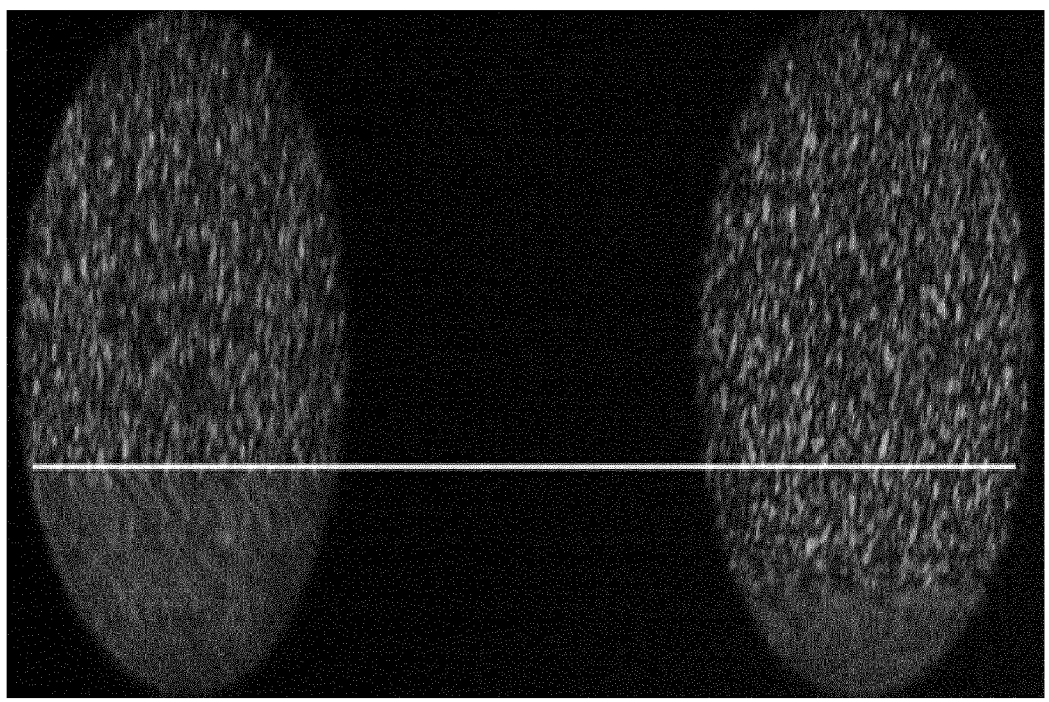

An example of such a scenario is illustrated in FIG. 6. The patterns are obtained from an experimental setup wherein a laser projects a pattern of two light spots on a piece of paper that is attached to a small loudspeaker emitting a pulse. By aligning the orientation of the reflected dots and the camera orientation, differences in the pulse arrival time can be observed as vertical shifts between the left and right pattern transitions.

As illustrated in FIG. 6, the speaker displacement causes severe pattern translations and motion blur in the bottom part of the left pattern. In the right pattern, the onset of the pulse can be observed at a different vertical position indicating the delay in arrival time of the pulse as the wave propagates from the position of one light spot to the position of the second light spot. The vertical displacement of the pattern, in turn, can be converted in a time delay using the line frequency. It should be noted that the camera alignment has no influence on the vertical position of the onset of the distortion due to object motion. The vertical onset of the distortion is only dependent on time.

The analysis processor 113 can in such an example detect the spatial position of the change occurring in the first speckle image and the spatial position of the change occurring in the second speckle image. This spatial offset can be estimated and converted to a time difference between the wave front passing the first and second light spots based on the rolling shutter propagation velocity. The wave velocity can then be calculated from the time difference and the distance between the light spots.

It will be appreciated that there are multiple ways of detecting the changes in the speckle patterns and to estimate the vertical spatial offset between the changes in adjacent speckle patterns. First of all, the two-dimensional image data can be converted into one-dimensional traces by tracking the line-to-line displacements and analyzing the resulting motion patterns. Alternatively, the speckle contrast may for each speckle pattern be determined for individual lines (or groups of N lines). The relative change between consecutive lines may then be evaluated and if the change exceeds a given threshold, a speckle pattern change may be considered to occur at that position. The spatial offset may then be determined as the number of lines between the detected change positions of the first and second speckle patterns.

As a more detailed example, the analysis processor 113 may be arranged to perform a line based analysis to determine the time difference and thus the wave velocity. Specifically, the camera may be arranged to sequentially sample a group of adjacent lines at a time followed by the next group of lines etc. Typically, the camera captures one line at a time, but in some embodiments it may capture N lines at a time where N is any integer. The total image is thus made up from a plurality of groups of adjacent lines captured at different times. The analysis processor 113 may in such embodiments proceed to compare the speckle patterns of different groups in order to detect when a change occurs. It will also be appreciated that in some embodiments, the speckle imaging apparatus 101 may generate the individual groups of lines by combining adjacent lines that are not captured simultaneously. For example, for a rolling shutter capturing one line a time, groups of lines used for the analysis may be formed by combining two, three or more lines. This will result in an effective decrease of spatial resolution in the direction of the rolling shutter propagation, and thus in a decreased temporal resolution, but may provide a more reliable evaluation of each group.

The following description will for brevity and clarity focus on examples wherein each group consist of one line and wherein the rolling shutter performs a line sequential capture of one line at a time. As a specific example, each group may comprise a single horizontal row.

In this case the analysis processor 113 can proceed to (for each speckle pattern) compare row speckle patterns of different rows to determine when a change occurs. Specifically, for each line and for each speckle pattern, the analysis processor 113 proceeds to determine a property of the speckle pattern.

The property may for example be an inter-line speckle pattern displacement. For example, the analysis processor 113 may correlate adjacent lines to determine an estimated pattern translation. It will be appreciated that averaging over multiple lines, filtering of generated movement estimations etc. may be applied.

In this approach, the speckle pattern is preferably generated to have relatively coarse speckle grains, and in particular to have speckle grains for which at least 80% of the speckles have an extension in the rolling shutter propagation direction (i.e. vertically in the specific example) which exceeds two lines (or 2N lines if the shutter captures N lines at a time).

Figure 7:
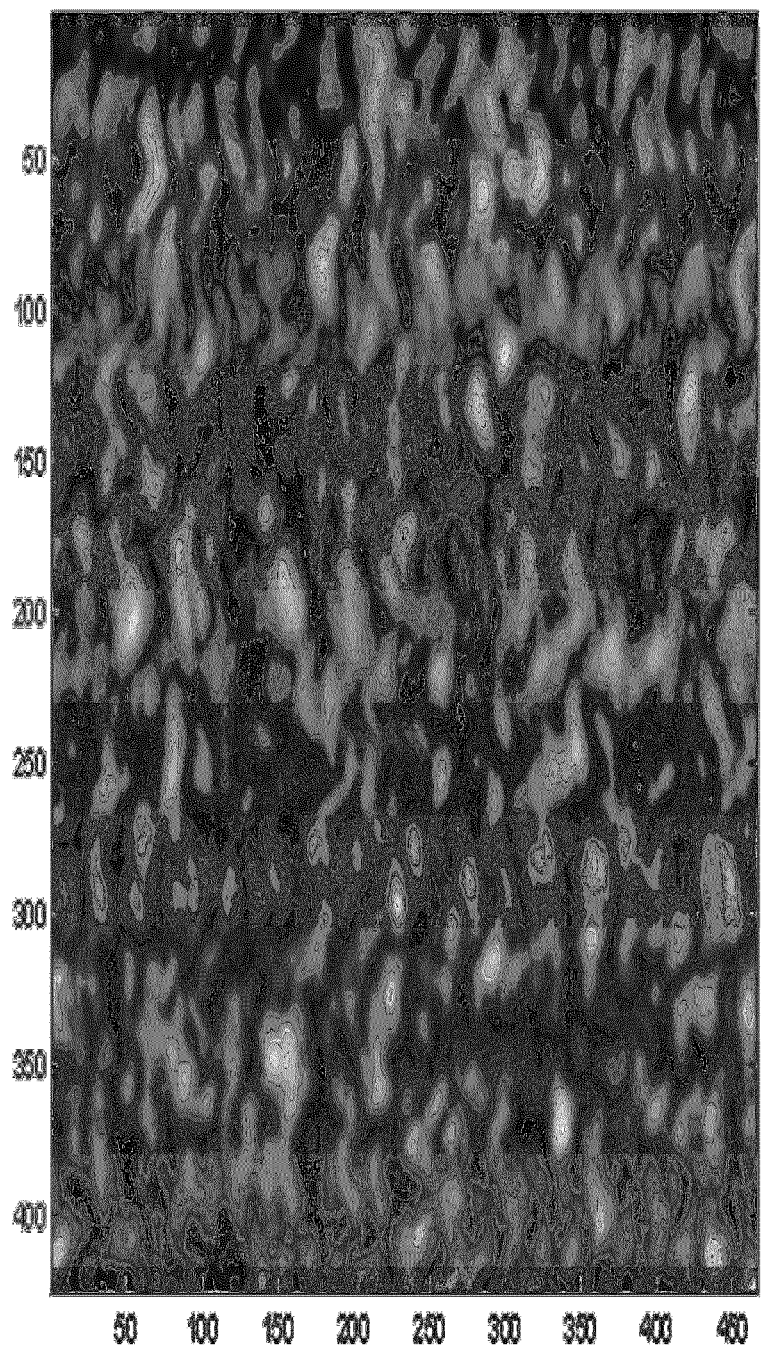
Figure 8:
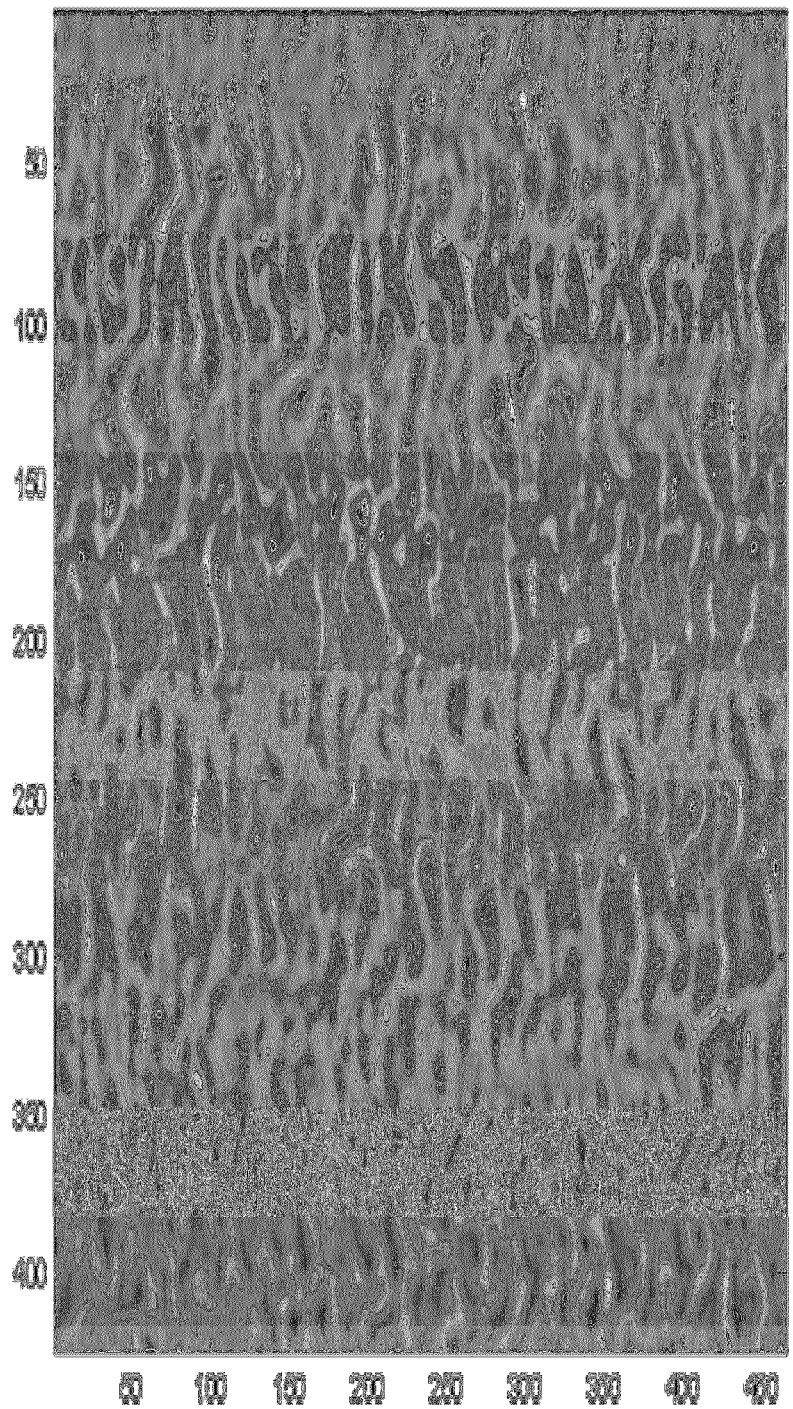
FIG. 8 illustrates an example of an edge enhanced speckle pattern.

As a specific example, FIG. 7 illustrates part of a speckle pattern for a surface of a piezoelectric sound transducer that is driven by an electric signal from a function generator. The speckle pattern clearly exhibits a wave-shaped distortion which becomes more visible after enhancement of vertical edges. FIG. 8 illustrates the speckle pattern after such an edge enhancement operation. It will be appreciated that the edge enhancement is optional and that the skilled person will be aware of many suitable edge enhancement algorithms. The enhanced image is then used as the input image for a row-by-row cross correlation operation which estimates the displacement between consecutive rows with sub-pixel accuracy.

Specifically, the displacement, dx, can be estimated using a line cross correlation according to:

$$dx(y) = \arg\max_d \sum_{\forall x} i_y(x) \cdot i_{y+1}(x+d)$$

where y is the line/row number, x in column number, and i indicates the pixel value.

Figure 9:
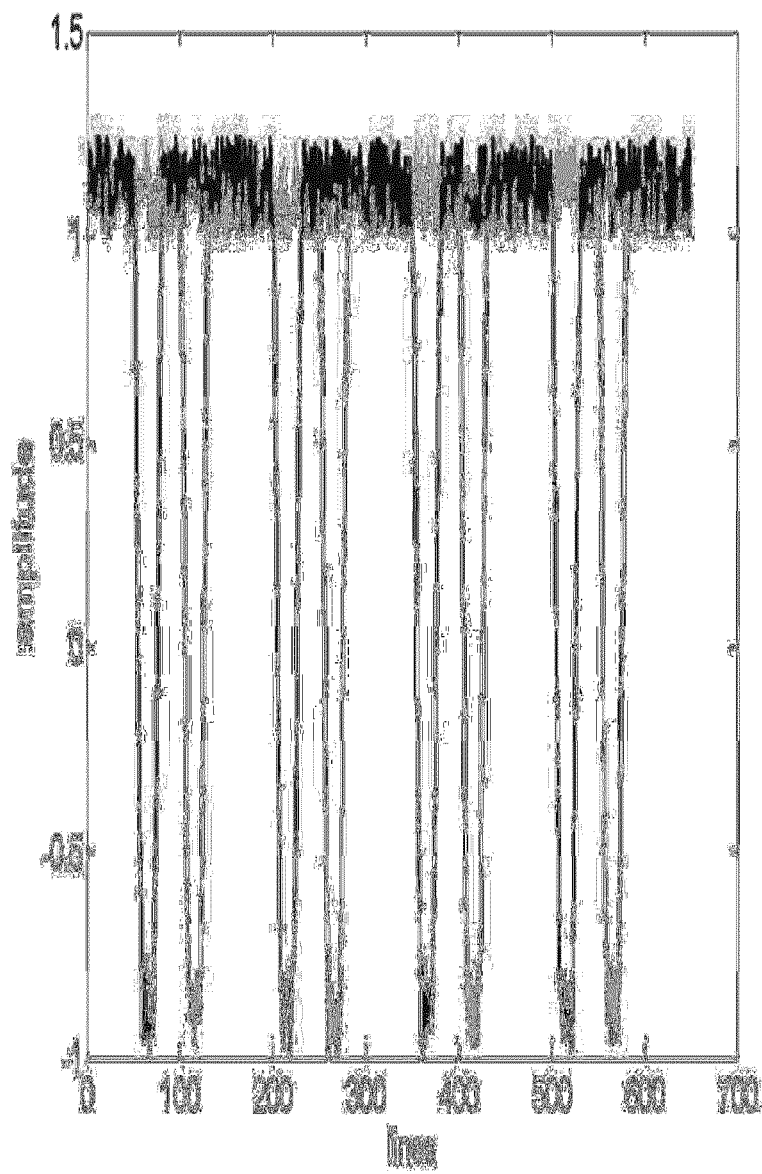
FIG. 9 illustrate an example of variations in a property of two speckle patterns.

The resulting displacements from applying this approach to the image of FIG. 8 are illustrated in FIG. 9. As can be seen, the estimated displacement directly corresponds to the sine wave motion of the surface.

As can be seen, the speckle pattern displacement between adjacent lines in the direction of the rolling shutter propagation is close to zero for no motion but changes to non-zero value when motion of the surface occurs. Accordingly, the detection of a change in the speckle pattern caused by the surface wave passing the corresponding light spot may be found as the line position for which the line-to-line translation exceeds a given threshold. The analysis processor 113 accordingly proceeds to determine the spatial position (specifically the line number) for which this occurs in relatively the first and second speckle pattern.

It will be appreciated that the analysis processor 113 may often apply a low pass filtering (e.g. a moving average) to the generated line-to-line displacement estimates before comparing them to a threshold. It will also be appreciated that in other embodiments more complex evaluations may be performed and more complex criteria may be applied.

As another example, the analysis processor 113 may determine the time difference in response to a spatial offset between corresponding changes in line speckle contrast for the two light spots.

Thus, in such embodiments, the analysis processor 113 may calculate a speckle contrast for each line of both the first and the second speckle patterns.

The speckle contrast C may for example be calculated as the ratio of the standard deviation σ of the intensity I to the mean intensity $I_{mean}$ of the speckle pattern:

$$C = \frac{\sigma}{I_{mean}}$$

The analysis processor 113 may accordingly calculate this value for each line of the image and for both the first and the second speckle patterns.

When a surface wave passes a light spot, the resulting motion of the speckle pattern will result in severe motion blur, which in turn reduces the speckle contrast considerably. Accordingly, the analysis processor 113 may proceed to detect the pulse wave by detecting the positions for which the speckle contrast decreases below a threshold.

Again it will be appreciated that the analysis processor 113 may apply filtering or averaging and indeed may apply more complex analysis and/or change detection criteria.

Once the spatial positions of the speckle patterns changes have been detected in the image, the analysis processor 113 can use the spatial offset to determine the time difference between the changes. Specifically the corresponding time difference can be calculated as the spatial offset (measured in lines) divided by the rolling shutter line frequency. The pulse wave velocity can then be calculated as the distance between the light spots divided by the time difference.

In the specific example, only speckle patterns of one image were considered. However, the comparison between the speckle patterns of the two light spots may be between speckle patterns in the same image/frame or may be between speckle patterns in different images. For example, when the time difference between the surface wave passing the first and second light spot is less than a frame time, the comparison may be performed between speckle patterns in the same image, and when it exceeds a frame time it may be performed between speckle patterns in different images. In some embodiments, the correlation may for example be applied between a speckle pattern for the first light spot in one image and the speckle pattern for the second light spot in a plurality of images (e.g. including the same image). The maximum overall correlation may be found and the time difference may be calculated as the inter-frame time offset corresponding to the spatial offset.

Furthermore, the previous example was based on determining the surface wave velocity from a single wave front. However, in many applications the surface wave is a repeating surface wave. Specifically, for a pulse wave measurement the surface wave is repeated for each beat of the heart. In some embodiments, this may be used to determine the time difference between changes in the two speckle patterns. This may for example be done by performing the above described operation for each repetition of the surface wave and then averaging the result (e.g. averaging the calculated velocity or e.g. the determined time difference).

As another example, a cross correlation between the determined speckle pattern property values may be extended over a plurality of repetitions of the surface wave. An example of a property determined for the two speckle patterns for a repeating surface wave is illustrated in FIG. 9.

The example specifically illustrates a speckle contrast value and as can be seen there is a clear and consistent spatial offset between the two light spots. This offset may be determined using techniques such as cross-correlation or by comparison of the positions of characteristic feature points, such as the occurrence of maxima and minima.

The system of FIG. 1 can thus exploit the rolling shutter effect to allow an accurate and high resolution determination of the pulse wave velocity. This can be achieved without requiring high speed cameras and indeed for many applications a simple standard low-cost mega-pixel camera is sufficient to provide both the spatial and temporal resolution required. Furthermore, as all analysis is based on images comprising both speckle patterns the need for complex and difficult synchronization between different equipment can be avoided.

In the previous examples, the light spots generated by the coherent light source 105 have been considered to be circular spots, and the capture of the circular spots has resulted in circular image objects. Such an approach is typically used for speckle imaging.

However, in some embodiments the speckle imaging apparatus 101 of FIG. 1 is arranged such that the speckle patterns captured by the image sensor of the camera 111 are anisotropic. Such non-circular speckle imaging may result in improved speckle patterns for a rolling shutter, and may in particular facilitate the analysis of the speckle patterns.

The anisotropic imaging may specifically be achieved by the coherent light source 105 being arranged to generate the light spots on the surface as anisotropic light spots. Thus, rather than generating circular light spots, the coherent light source 105 generates light spots which may e.g. be elliptical.

Indeed, the size of the speckles in the speckle patterns is inversely related to the laser spot size, such that the smaller the spot size, the coarser the speckles. The inventors have realized that this consideration can also be applied to each dimension separately to obtain an anisotropic speckle pattern, and that this is particularly beneficial when using a rolling shutter capture. In particular, an anisotropic light spot can be used to increase the vertical correlation of the speckle pattern (i.e. in the rolling shutter propagation direction) while maintaining a fine horizontal displacement resolution (i.e. in the perpendicular direction).

The speckle patterns can for example be controlled by the lens 109 of the speckle imaging apparatus 101 of FIG. 1 being a cylindrical lens. This will result in elliptical light spots. If the major axis of the light spot ellipse is oriented horizontally (i.e. aligned with a direction perpendicular to the rolling shutter propagation direction, and in the specific example aligned with the image sensor column direction), this will result in speckles which are elongated in the vertical direction (i.e. aligned with the rolling shutter propagation direction, and in the specific example aligned with the image sensor row direction). This approach may provide a higher correlation between lines while maintaining the high resolution and speckle variation of each line. This may result in improved detection of changes in the speckle pattern and in particular in improved detection based on inter-line displacements.

Figure 10:
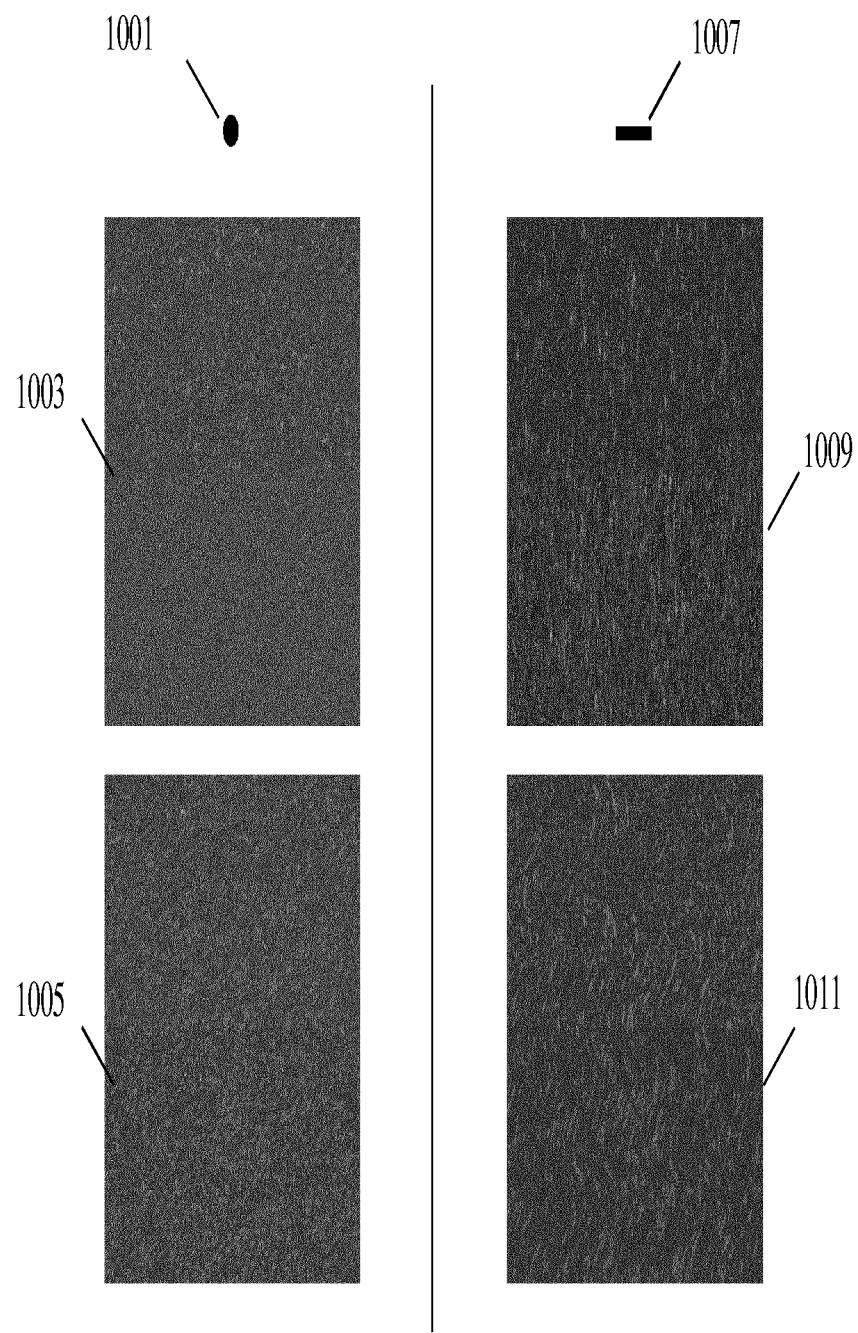
FIG. 10 illustrates examples of speckle patterns for isotropic and anisotropic speckle patterns.

The effect is illustrated in FIG. 10 which shows a comparison between corresponding speckle patterns for an isotropic and non-isotropic light spot for respectively no motion and a surface sinusoidal motion.

FIG. 10 specifically shows a speckle pattern of an anisotropic light spot 1001 captured with a rolling shutter camera when there is no motion (pattern 1003) and when there is a high-frequency surface motion (pattern 1005). It further shows a speckle pattern of an isotropic light spot 1007 captured with a rolling shutter camera when there is no motion (pattern 1009) and when there is a high-frequency surface motion (pattern 1011).

As can be seen, the isotropic light spot results in an isotropic speckle pattern wherein the motion information (corresponding to the horizontal line shifts) is hard to discern. However, for the anisotropic light spot, the speckles are elongated resulting in the motion information being much easier to detect. In the example, the anisotropic light spot 1007 has been extended in the horizontal direction relative to the isotropic light spot 1001. This clearly results in an increased vertical dimension of the speckles and thus provides a higher line to line correlation. At the same time, the horizontal resolution is maintained.

It will be appreciated that the exact anisotropicity of the light spots will depend on the specifics of the individual embodiment. However, in many embodiments the average extension of the speckle grains in a direction corresponding to the rolling shutter propagation direction are at least twice that of the average extension of the speckle grains in a direction perpendicular thereto. Thus, in many embodiments, the anisotropic light spot image (or indeed the light spot itself) may have a longest dimension which is at least twice that of the shortest dimension.

The anisotropic speckle patterns need not be generated by anisotropic light spots on the surface. Rather, in some embodiments, the coherent light source 105 may be arranged to generate the light spots as isotropic light spots with the camera 111 being arranged to generate the corresponding speckle patterns as anisotropic light spot image objects.

Thus, in some embodiments the imaging optics may be modified instead of the projection optics. This may for example be achieved by the use of an anisotropic optical aperture, astigmatic optics, anamorphic optics, or prisms. Indeed, by changing the imaging optics, it is possible to stretch the image more in one direction than in another. This can affect both the outline of the blur circle and the shape of the (observed) speckles.

Specifically, may be done similarly to the use of anamorphic lenses in film recording and cinema projection in order to obtain ultra wide screen images by change of the aspect ratio in the capture and/or projection elements. The optics might include cylindrical lenses or curved mirrors.

In the example, the anamorphic optics would be oriented such that the speckles are relatively stretched in the propagation direction of the rolling shutter.

The previous embodiments have focused on examples wherein the coherent light source 105 generates only two light spots which then each create a speckle pattern image object to be analyzed. However, in some embodiments, the coherent light source 105 can be arranged to generate more than two light spots on the surface.

Figure 11:
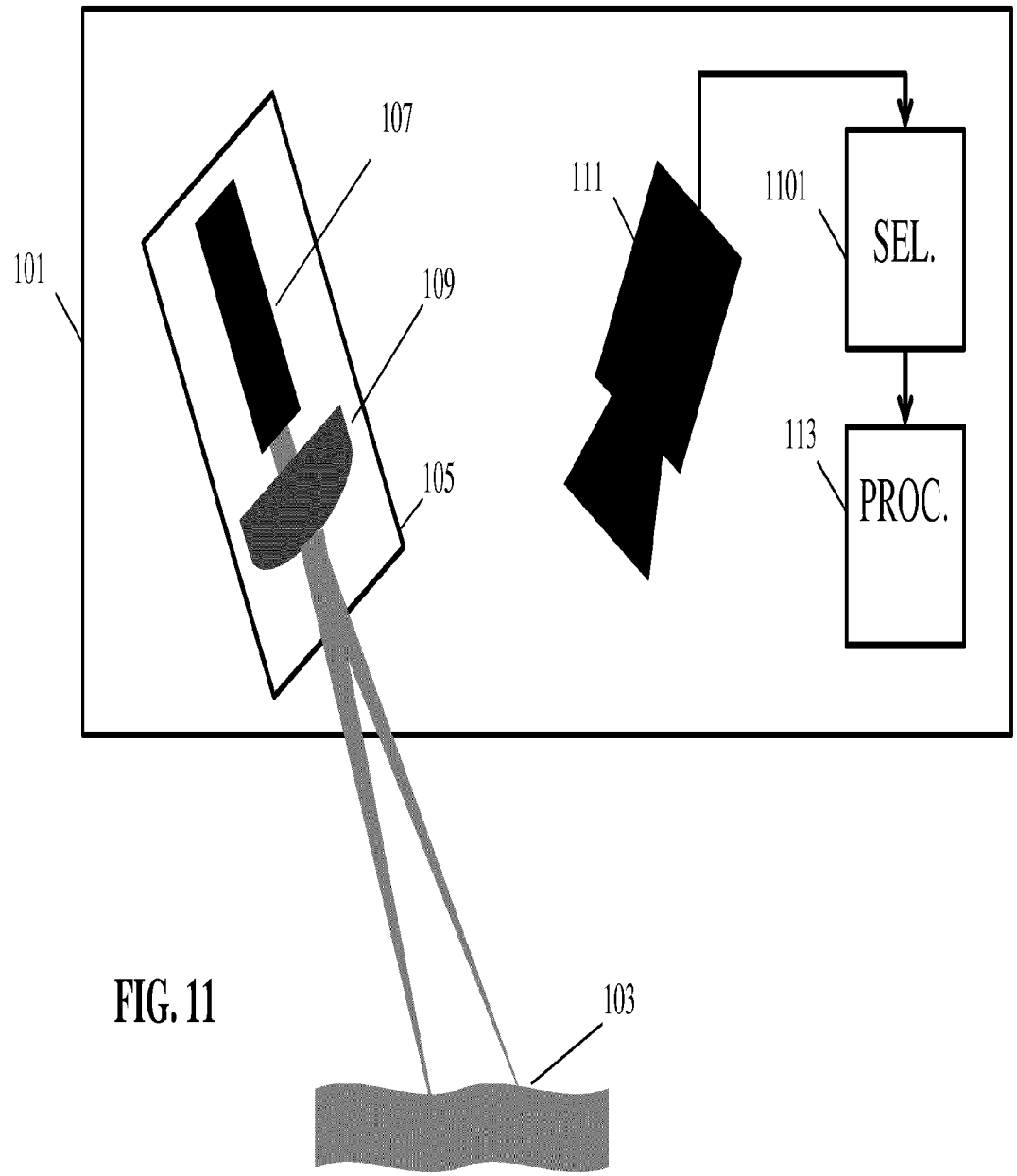
FIG. 11 illustrates an example of a speckle imaging apparatus in accordance with some embodiments of the invention.

Such an exemplary embodiment is illustrated in FIG. 11. The example corresponds to the example of FIG. 1 but with the coherent light source 105 generating more than two light spots. This may for example be achieved by the use of multiple laser light sources, a single source with a diffraction grating, or the use of beam splitters and mirrors.

The camera 111 is arranged such that it captures all of the light spots. The speckle imaging apparatus 101 furthermore includes a selector 1101 which is arranged to select a subset of at least two of the plurality of light spots. The selector 1101 is furthermore coupled to the analysis processor 113 which proceeds to analyze the speckle patterns of the subset of light spots.

The approach may be particularly suitable for automatic or semi-automatic adaptation to the specific positioning of the surface/tissue, and may in particular provide an increase flexibility and freedom in positioning the object to be monitored.

For example, the plurality of light spots may form a regular or non-regular grid. An object to be measured may then be placed within a relatively coarse test area, and the system may evaluate the plurality of light spots to find two or more of the light spots which are located at suitable positions on the surface. The analysis may then be based on the selected light spots. Furthermore, by performing a selection of a subset of light spots prior to the detailed analysis, a more efficient and less resource demanding system can be achieved.

Thus, the approach may use the projection of multiple light spots, e.g. in a regular pattern, to increase the likelihood of illuminating an interesting part of the tissue (e.g. of a patient) to be measured. Furthermore, from the set of light spots a subset can be selected by selecting a region of interest on the camera sensor. The spatial resolution and frame rate can then be increased e.g. by only capturing and processing the selected region of interest.

In many applications, the likelihood of illuminating a preferential or even suitable spot on the subject or object under study without performing a manual adaption or requiring a very specific placement of the object is very small. Indeed, in most applications it is required that the analyzed light spot is positioned on an area of the surface wherein e.g. suitable vibrations are experienced. Typically, this is a relatively small area and the two light spots must be positioned carefully. However, by using more light spots, only a coarse and flexible positioning of the object to be monitored relative to the coherent light source 105 (and camera) is required, and the speckle imaging apparatus 101 can then automatically adapt and select light spots positioned at suitable positions of the surface.

A disadvantage of observing multiple light spots, however, is that the amount of information increases which may increase the resource demand and processing required. However, by having a separate selection of suitable spots for analysis, this may be mitigated and the resulting increase computational demands may be kept very low. For example, the spatial or temporal resolution may be decreased. For example, the spatial sensor resolution may be reduced by binning or sub sampling. As another example, the temporal resolution may be decreased by using a lower frame rate, e.g. by skipping frames when performing the selection. Furthermore, once a subset of light spots has been identified, these may be analyzed with full pixel resolution and frame rate thereby ensuring that there is no degradation in the estimation of the surface motion.

As an example, a two megapixel sensor with a frame rate of 12 frames per second at full resolution may be used for the selection. However, when performing the full analysis only the small area corresponding to e.g. one selected light spot image object may be selected. This may allow a much faster frame rate, such as e.g. 200 frames per second.

Figure 12:
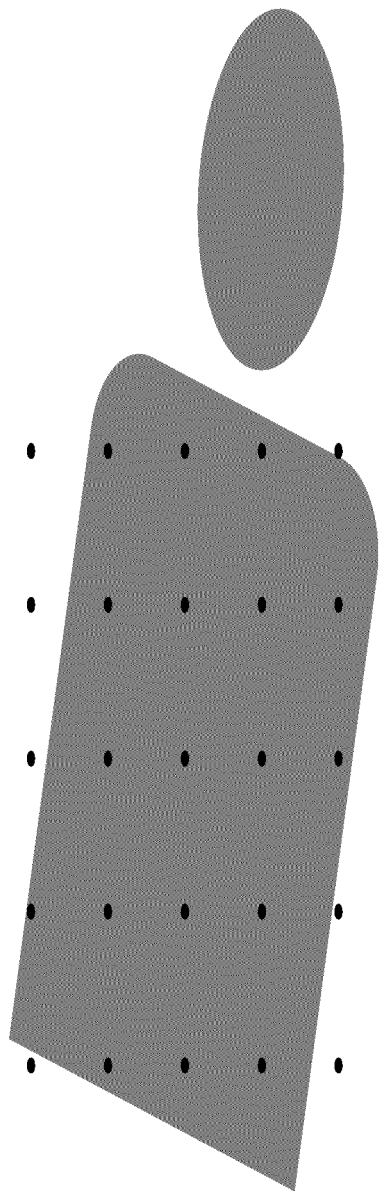
FIGS. 12 to 14 illustrate examples of speckle pattern imaging using a grid of light spots.

As a specific example, the speckle imaging apparatus 101 may be used to determine a pulse wave velocity for a patient. The coherent light source 105 may generate a grid of light spots as illustrated in FIG. 12. The setup can for example be positioned above a patient bed where the light spot pattern overlaps with the chest area of a resting patient. The pattern does not have to be visible but may e.g. be based on invisible infra-red illumination and sensing. A lens or set of lenses is not necessary for the projection but can improve the signal quality as the speckle coarseness and hence effective contrast is related to the size of the laser spots.

Figure 13:
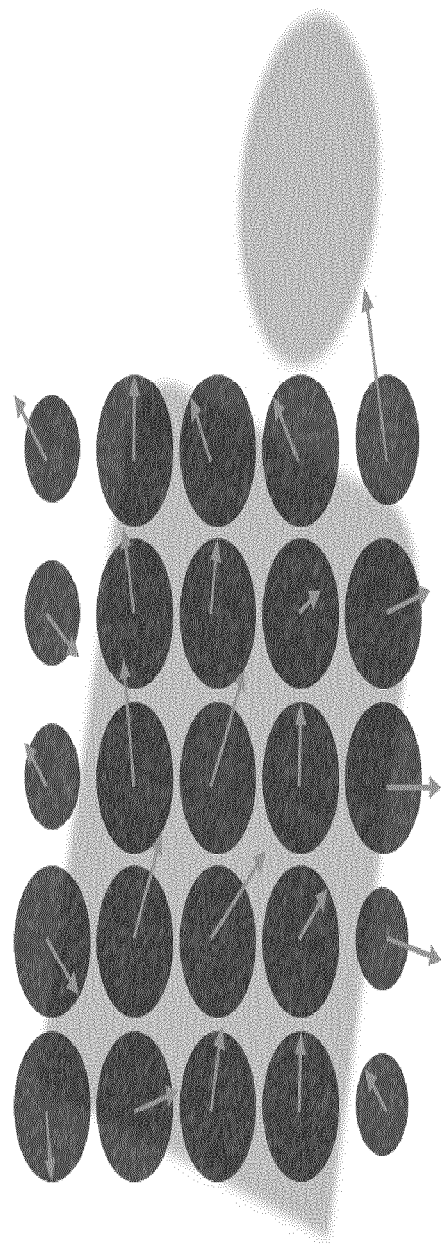
Figure 14:
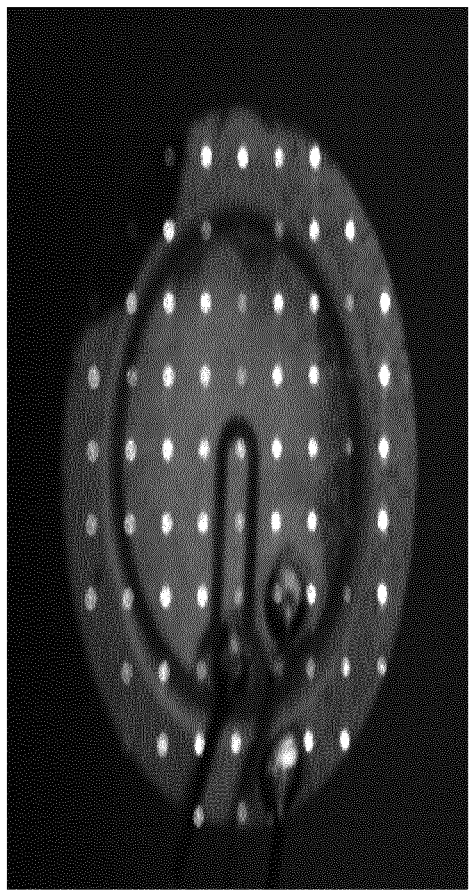
Figure 14:
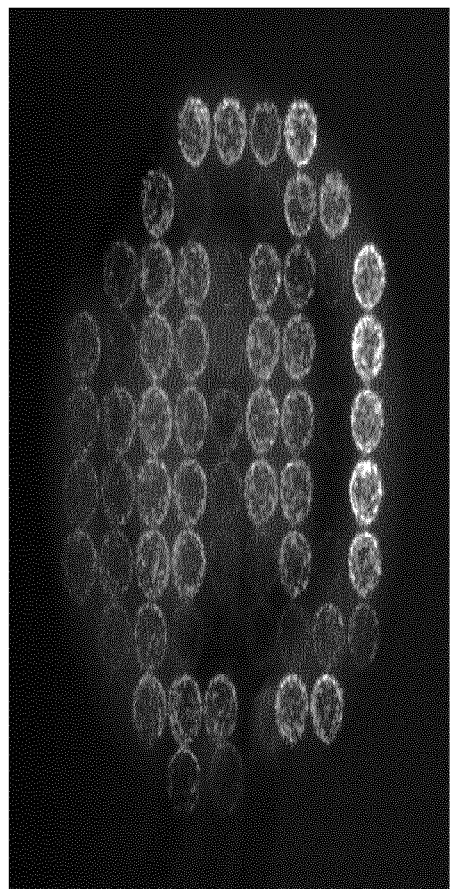

FIG. 13 illustrates the image that may be captured by the out-of-focus camera 111. As can be seen a speckle pattern is generated for each light spot. FIG. 14 illustrates corresponding images captured for an experimental setup wherein the surface is a surface of a piezoelectric transducer, The example of FIGS. 12 and 13 may specifically be used for remote measurement of the pulse wave velocity of a patient. When the heart beats, small disturbances can be detected on the skin surface of the patient, for example on the chest of the patient (or e.g. on the arm, neck etc.). In the example, the analysis of the speckle patterns may thus provide information of the pulse wave velocity for a patient. However, in order to provide reliable estimates, it is important that the light spots used to determine the velocity are positioned appropriately.

Therefore, in order to increase the accuracy of the pulse wave velocity estimate, the system is arranged to select two of the light spots. Following the selection of the subset (which corresponds to a smaller area of the image sensor), the spatial resolution (of the sensor) and frame rate/temporal resolution can be increased for more accurate measurements. It should be borne in mind that the spatial resolution does not just indicate the total number of pixels but the number of pixels per unit length or resolving power.

The exact algorithm and criteria used for selecting the subset will depend on the preferences and requirements of the individual embodiment.

In some embodiments, the selector 1101 may be arranged to select the subset in response to intensity of light spots of the light spots in the out-of-focus image. As can be seen from FIG. 14 the intensity of the light spots in the out-of-focus image varies for different light spots. In particular, the average brightness for a light spot image object in the out-of-focus image may depend on the reflection properties of the reflecting surface and this may be used to ensure that the selected light spots are indeed from the appropriate surface. Therefore, the subset may be selected to comprise the light spots that have a high intensity thereby resulting in improved analysis.

In some embodiments, the selector 1101 may be arranged to select the subset in response to a speckle contrast of light spots of the plurality of the light spots. As illustrated in FIG. 14, the speckle contrast may depend on the exact properties associated with the specific position of the light spot. For example, if the distance to the light spot deviates from the exact focus distance, the speckle pattern may become coarser and may result in a reduced contrast. By selecting the subset of light spots to have a high speckle contrast, an improved analysis can be performed. E.g. a correlation estimation may become more accurate and reliable.

In some embodiments, the selector 1101 may be arranged to select the subset in response to a speckle pattern variation of light spots of the plurality of the light spots. In particular, the subset may be selected based on correlations between speckle patterns of different light spots. Thus, in some embodiments, the selector 1101 may be arranged to select the subset in response to a correlation between variations of different light spots of the plurality of the light spots.

In some embodiments, the subset may be selected in response to the speckle pattern variations having a temporal behavior which meets a similarity criterion. For example, the subset may be selected to only include light spots for which the speckle patterns change at substantially corresponding but perhaps with a time offset, or which e.g. have repeating variations with the same frequency. For example, when monitoring a pulse wave, this can ensure that only light spots positioned on surfaces which move with the pulse of the patient are considered.

In some embodiments, the variation of the speckle pattern may be measured as a motion estimate for the speckle pattern. Specifically low complexity motion estimation may be performed and used to select light spots that have corresponding motions.

In some embodiments, the selector 1101 may be arranged to select the subset in response to a change in a light spot pattern of the light spots. Specifically, the coherent light source 105 may be arranged to generate a regular grid of light spots. However, when the grid covers an area with significant depth variations (e.g. both the patient's chest and part of the hospital bed), the depth distances result in a relative displacement of the light spots in the captured image. Thus, a non-regular grid may be recorded in the captured image, and this deviation may be used to identify light spots that do not have the expected depth. This approach may for example be used to detect which light spots hit the patient's chest.

In some embodiments, the selector 1101 may be arranged to select the subset in response to a non-speckle pattern image. For example, the light spot positions relative to the positioning of the patient may be evaluated using another image. This image may for example be an in-focus image which may show the light spots as small spots together with the patient and part of the bed. The system may then evaluate which spots are overlaying the patient's chest. As other examples, the relation of the spot positions to the patient position might be derived from an additional camera image, the background image, or prior information.

It will be appreciated that the subset selection need not be performed for every frame of a video based imaging system. For example, the subset selection may be repeated at given time intervals. For example, reselecting the light spots for the subset every couple of seconds would allow the system to track patient movements.

In some embodiments, the system may comprise feedback functionality which may for example control the coherent light source to switch some of the light spots on and off. Also, whereas the regular grid of substantially identical light spots may often be used, the system can also be used with a non-uniform grid. Indeed, not only may the grid spacing vary but so may the light spot sizes. This may be used to optimize the monitoring for the specific characteristics of the application.

It will also be appreciated that whereas the use of multiple light spots may be particularly suitable for rolling shutter speckle imaging, it may also be suitable for many other speckle imaging types and applications.

It will be appreciated that the approach may specifically be used to estimate pulse wave velocity measurements, and accordingly can provide unobtrusive blood pressure estimates. These can be used for diverse medical applications, such as neonatal monitoring or continuous (home) patient monitoring for patients suffering from cardiological disease.

It will also be appreciated that the general principles can be used to estimate other types of wave propagation along the targeted surface, which may find industrial applications, such as vibration monitoring for production equipment.

It will be appreciated that the above description for clarity has described embodiments of the invention with reference to different functional circuits, units and processors. However, it will be apparent that any suitable distribution of functionality between different functional circuits, units or processors may be used without detracting from the invention. For example, functionality illustrated to be performed by separate processors or controllers may be performed by the same processor or controllers. Hence, references to specific functional units or circuits are only to be seen as references to suitable means for providing the described functionality rather than indicative of a strict logical or physical structure or organization.

The invention can be implemented in any suitable form including hardware, software, firmware or any combination of these. The invention may optionally be implemented at least partly as computer software running on one or more data processors and/or digital signal processors. The elements and components of an embodiment of the invention may be physically, functionally and logically implemented in any suitable way. Indeed the functionality may be implemented in a single unit, in a plurality of units or as part of other functional units. As such, the invention may be implemented in a single unit or may be physically and functionally distributed between different units, circuits and processors.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term "comprising" does not exclude the presence of other elements or steps.

Furthermore, although individually listed, a plurality of means, elements, circuits or method steps may be implemented by e.g. a single circuit, unit or processor. Additionally, although individual features may be included in different claims, these may possibly be advantageously combined, and the inclusion in different claims does not imply that a combination of features is not feasible and/or advantageous. Also the inclusion of a feature in one category of claims does not imply a limitation to this category but rather indicates that the feature is equally applicable to other claim categories as appropriate. Furthermore, the order of features in the claims do not imply any specific order in which the features must be worked and in particular the order of individual steps in a method claim does not imply that the steps must be performed in this order. Rather, the steps may be performed in any suitable order. In addition, singular references do not exclude a plurality. Thus references to "a", "an", "first", "second" etc. do not preclude a plurality. Reference signs in the claims are provided merely as a clarifying example shall not be construed as limiting the scope of the claims in any way.

The invention claimed is:

1. An apparatus for determining a propagation velocity for a surface wave, the apparatus comprising:
   a coherent light source for generating at least a first light spot and a second light spot substantially simultaneously on a surface wherein the first light spot and the second light spot are spatially separated;
   a camera for capturing at least one out-of-focus image of at least a part of the surface comprising the first and second light spots, the out-of-focus image comprising a first light spot image object for the first light spot, and a second light spot image object for the second light spot, the first light spot image object having a first speckle pattern, and the second light spot image object having a second speckle pattern;
   an analyzer for determining the propagation velocity in response to a time difference between speckle pattern changes in the first speckle pattern and the second speckle pattern; and
   wherein the analyzer is arranged to determine the time difference between speckle pattern changes in the first speckle pattern and the second speckle pattern in response to a spatial comparison of the first speckle pattern and the second speckle pattern in one out-of-focus image captured by the camera, wherein the camera comprises a rolling shutter for capturing the at least one out-of-focus image.

2. The apparatus of claim 1, wherein the analyzer is arranged to:
   determine a property of the first speckle pattern;
   determine a property of the second speckle pattern;
   detect a change in the property of the first speckle pattern;
   detect a change in the property of the second speckle pattern; and
   determine the propagation velocity in response to a time difference between a time instant of the change in the property of the first speckle pattern and a time instant of the change in the property of the second speckle pattern.

3. The apparatus of claim 1, wherein the analyzer is arranged to determine the time difference in response to a spatial correlation of the first speckle pattern and the second speckle pattern.

4. The apparatus of claim 1, wherein the analyzer is arranged to determine the time difference in response to a spatial pattern variation for the first speckle pattern and the second speckle pattern in a direction corresponding to the rolling shutter propagation direction.

5. The apparatus of claim 1, wherein the analyzer is arranged to determine the time difference in response to a spatial offset between pattern changes in the first speckle pattern and the second speckle pattern.

6. The apparatus of claim 1, wherein the rolling shutter is arranged to capture the out-of-focus image line sequentially; and the analyzer is arranged to:
   determine a speckle pattern property for the first light spot image object for each group of a plurality of groups which each comprise at least part of a number of adjacent lines of the out-of-focus image;
   determine a speckle pattern property for the second light spot image object for each group of the plurality of groups;
   detect a change of the pattern property for the first light spot image between groups of the plurality of groups;
   detect a change of the pattern property for the second light spot image between groups of the second plurality of groups; and
   determine the time difference in response to a spatial difference between the change of the pattern property in the first light spot image object and the change of the pattern property in the second light spot image object.

7. The apparatus of claim 1, wherein the analyzer is arranged to determine the time difference in response to a spatial offset between changes in speckle contrast for the first light spot image object and the second light spot image object.

8. The apparatus of claim 1, wherein the analyzer is arranged to determine the time difference in response to a spatial offset between changes in inter-line speckle pattern displacements for the first light spot image object and the second light spot image object.

9. The apparatus of claim 1, wherein the coherent light source is arranged to generate a plurality of light spots on the surface and the camera is arranged to capture the plurality of light spots in the out-of-focus image; and the apparatus further comprising:
   a selector arranged to select a subset of light spots for analysis by the analyzer.

10. The apparatus of claim 9, wherein the selector is arranged to select the subset of light spots using a lower processing resolution than used by the analyzer when determining the propagation velocity.

11. The apparatus of claim 9, wherein the selector is arranged to select the subset in response to at least one of:
   an intensity for light spots of the plurality of the light spots;
   a speckle contrast for light spots of the plurality of the light spots;
   a speckle pattern variation for light spots of the plurality of the light spots;
   a correlation between variations for different light spots of the plurality of the light spots; and
   a change in a light spot pattern of the plurality of the light spots.

12. The apparatus of claim 1, arranged to determine a propagation velocity for a pulse wave.

13. A method of determining a propagation velocity for a surface wave, the method comprising:
   generating by a coherent light source at least a first light spot and a second light spot substantially simultaneously on a surface wherein the first light spot and the second light spot are spatially separated;
   capturing by a camera at least one out-of-focus image of at least a part of the surface comprising the first and second light spots, the out-of-focus image comprising a first light spot image object for the first light spot, and a second light spot image object for the second light spot, the first light spot image object having a first speckle pattern, and the second light spot image object having a second speckle pattern;
   determining the propagation velocity in response to a time difference between speckle pattern changes in the first speckle pattern and the second speckle pattern; and
   wherein the determining of the propagation velocity comprises determining the time difference between speckle pattern changes in the first speckle pattern and the second speckle pattern in response to a spatial comparison of the first speckle pattern and the second speckle pattern in one out-of-focus image, wherein said out-of-focus image is captured by a camera comprising rolling shutter for capturing the at least one out-of-focus image.

\* \* \* \* \*